US006534271B2

(12) United States Patent
Fürste et al.

(10) Patent No.: US 6,534,271 B2
(45) Date of Patent: Mar. 18, 2003

(54) CLONING AND COPYING ON SURFACES

(75) Inventors: Jens Peter Fürste, Berlin (DE); Sven Klussmann, Berlin (DE); Thomas Klein, Berlin (DE); Günter Von Kiedrowski, Bochum (DE)

(73) Assignee: Noxxon Pharma AG, Berlin (DE)

( * ) Notice: Subject to any disclaimer, the term of this patent is extended or adjusted under 35 U.S.C. 154(b) by 0 days.

(21) Appl. No.: 09/866,513

(22) Filed: May 25, 2001

(65) Prior Publication Data

US 2002/0022275 A1 Feb. 21, 2002

Related U.S. Application Data

(63) Continuation-in-part of application No. PCT/DE99/03856, filed on Nov. 26, 1999.

(30) Foreign Application Priority Data

Nov. 27, 1998 (DE) .......................................... 198 54 946

(51) Int. Cl.[7] .......................... C12Q 1/68; C12P 19/34; G01N 33/53
(52) U.S. Cl. ........................... 435/6; 435/7.1; 435/91.2
(58) Field of Search .......................... 435/6, 91.1, 91.2, 435/7.1; 436/94

(56) References Cited

U.S. PATENT DOCUMENTS

| 4,458,066 A | 7/1984 | Caruthers et al. |
| 4,683,195 A | 7/1987 | Mullis et al. |
| 4,683,202 A | 7/1987 | Mullis |
| 5,424,186 A | 6/1995 | Fodor et al. |
| 5,445,934 A | 8/1995 | Fodor et al. |
| 5,489,678 A | 2/1996 | Fodor et al. |
| 5,510,270 A | 4/1996 | Fodor et al. |
| 5,641,658 A | 6/1997 | Adams et al. |
| 5,700,637 A | 12/1997 | Southern |
| 5,795,714 A | 8/1998 | Cantor et al. |
| 6,103,463 A | * 8/2000 | Chetverin et al. ............. 435/6 |
| 6,280,950 B1 | * 8/2001 | Lipshutz et al. ............... 435/6 |

FOREIGN PATENT DOCUMENTS

| EP | 0374665 | 6/1990 |
| WO | 9317126 | 9/1993 |
| WO | 9429484 | 12/1994 |
| WO | 9601836 | 1/1996 |
| WO | 9604404 | 2/1996 |

(List continued on next page.)

OTHER PUBLICATIONS

Systematic Functional Analysis of the Yeast Genome, Stephen G. Oliver, Michael K. Winson, Douglas B. Kell and Frank Baganz, T/B Tech, Sep. 1998, vol. 16, pp. 373–378.
"RNA–catalysed carbon—carbon bond formation," Theodore M. Tarasow, Sandra L. Tarasow, and Bruce E. Eaton, Nature, vol. 389, pp. 54–57.

(List continued on next page.)

Primary Examiner—Kenneth R. Horlick
(74) Attorney, Agent, or Firm—Nils H. Ljungman & Associates

(57) ABSTRACT

The present invention provides for amplification methods for cloning and copying genetic material on surfaces as well as copying biological material insofar as, in a broader sense, it can be classified as a ligand-receptor system. The invention therefore relates in particular to a method for propagating ligands and receptors on at least two surfaces, comprising (a) immobilizing a first ligand on a first surface of a substantially solid phase; (b) adding a solution of receptors and binding complementary receptors to the first ligand; (c) transferring the receptor to a second surface and immobilizing the receptor at that location; (d) attaching an additional ligand to the immobilized receptor; and (e) transferring the additional ligand to the first surface and immobilizing it at that location, wherein the steps set forth above may be repeated, multiple times.

22 Claims, 16 Drawing Sheets

FOREIGN PATENT DOCUMENTS

| WO | 9706468 |   | 2/1997 |
|----|---------|---|--------|
| WO | 9707243 |   | 2/1997 |
| WO | 9809735 |   | 3/1998 |
| WO | 9814610 |   | 4/1998 |
| WO | 9820019 |   | 5/1998 |
| WO | 99/19341 | * | 4/1999 |
| WO | 00/27521 | * | 5/2000 |

OTHER PUBLICATIONS

"Macromolecular matchmaking: advances in two–hybrid and related technologies," Robert M. Frederickson, Analytical Biotechnology, pp. 90–96.

"Automated DNA Sequencing and Anaylsis," Mark D. Adams, ed.

"Cloning Differentially Expressed mRNAs," Jackson S. Wan, et al., Nature Biotechnology, vol. 14, pp. 1685–1691.

"Present State and Frontiers in Biosensories," F.W. Scheller, E. Schubert, and J. Ecdrowitz, pp. 1–9.

"Why pharmacogenomics? Why now?, " David Housman and Fred D.Ledley, Nature Biotechnology, vol. 16, pp. 492–493.

"Light–Directed Spatially Addressable Parallel Chemical Synthesis," Stephen P.A. Foder, et al., Research Article, pp. 767–773.

"Surface–promoted replication and exponential amplification of DNA analogues," A. Luther, et al., Nature, vol. 396, pp. 245–248.

* cited by examiner (1)  (2)  (3)  (4)  (5)

(1)    (2)    (3)    (4)    (5)

(1)  (2)  (3)  (4)  (5)  (6)

(7)  (8)  (9)  (10)  (11)

(1) (2) (3) (4) (5) (6)

(7) (8)

(1)  (2)  (3)  (4)  (5)

CLONING AND COPYING ON SURFACES

CONTINUING APPLICATION DATA

This application is a Continuation-In-Part application of International Patent Application No. PCT/DE99/03856, filed on Nov. 26, 1999, which claims priority from Federal Republic of Germany Patent Application No. DE 198 54 946.6, filed on Nov. 27, 1998. International Application No. PCT/DE99/03856 was pending as of the filing date of the above-cited application. The United States was an elected state in International Application No. PCT/DE99/03856.

BACKGROUND OF THE INVENTION

1. Field of the Invention

This invention relates to a method for cloning and copying genetic material on surfaces as well as copying biological material insofar as it can be classified in a broader sense in a ligand-receptor system.

2. Background Information

Methods of exponentially amplifying molecular matrices are already known through the work of G. von Kiedrowski et al. (Nature 1998, Vol. 346, 245–248; Federal Republic of Germany Patent No. 198 48 403). The amplification cycles are characterized by:

- binding of molecular matrices to the surface of a solid phase by means of a reversible linker on the matrix;
- addition of matrix fragments, with one of the fragments displays a linker unit, which may, if necessary, be protected;
- synthesizing copies of the matrix;
- removal of superfluous matrix fragments and ancillary reaction substances;
- detachment of the copies from the matrix; and
- application of synthesized matrix copies to free binding sites on the solid phase.

This represents an iterative, progressive amplification method, allowing an exponential increase in the amount of molecular matrices available, thus enabling a significant process of evolution to take place. To achieve this the process makes use of the surface of a solid carrier. Chemical attachment to immobilized matrices enables copies to be synthesized from precursor matrices, which are then released to become new matrices. This process can be repeated any number of times.

In addition, so-called "bridge" amplification technology is described in U.S. Pat. No. 5,641,658. This is an amplification model based on conventional PCR methods, but which is intended to achieve localized amplification. Bridge amplification technology has many uses, especially in analytical methods that can also be carried out with the commonly used PCR. The bridge technology facilitates the separation and detection stages of the amplified products. The characteristics of this technology are that it combines amplification, selection and detection in a single process. Advanced state of the art systems can be found on the homepage of MOSAIC Technologies, Inc. (USA), the company marketing bridge amplification technology (www.mostek.com).

The bridge system describes a method for amplifying nucleic acids on a solid phase, with both amplification primers being bound covalently to a single solid phase through their 5' ends. Consequently this represents a further development of the well-known polymerase chain reaction, known as PCR for short. This takes place in a solid phase PCR instead of in a solution. The particular advantage of this method is its ability to amplify and analyze many different genetic elements simultaneously using a single sample. The applications for bridge amplification technology include genetic expression, genome research, clinical diagnostics and the examination of biological fluids, e.g. blood. A higher rate of amplification is achieved by eliminating ineffective primer artifacts (such as primer dimers). This enables simple, sensitive and cost-effective DNA detection methods to be developed, for example using fluorescence. Because bridge amplification technology ensures that all amplification products remain bound to the solid phase, contamination through prolongation remains low, and this in turn enhances the diagnostic value of the method compared with the usual PCR.

Whereas the method proposed by G. von Kiedrowski et al. referred to above demonstrates the benefits of the solid phase amplification of entire populations, the method described in U.S. Pat. No. 5,641,658 offers the advantage of amplifying a single matrix on a solid phase. However, the drawback of this bridge amplification method is linked with the problem of product inhibition, i.e. a newly produced copy may occur not only with the adjacent immobilized primer, but also with the original matrix strand, which is also adjacent. Another disadvantage is the lower linear limitation needed to achieve bridging as a double strand. Furthermore, there is no separation between the strands, with the result that, for diagnostic purposes, the hybridization signals are weakened due to hybridization with complementary strands.

Federal Republic of Germany Patent No. 694 09 646 T2 describes a method for amplifying a nucleic acid, in which the one primer is bound to a solid phase and the second primer to a particle that reacts with a magnetic field. These primers are incorporated in target nucleic acid sequences. Following an extension stage the nucleic acid strands are separated by the application of an electric current. The magnetic primer can be particle-bonded, existing as a form of solid phase. The avidin/biotin system is suitable for binding the primer to the solid phases. This method is also suitable for cloning.

U.S. Pat. No. 5,795,714 describes a method which, in one form, uses an array of oligonucleotides, which are connected to the surface of the solid phases by means of the reciprocal reaction between biotin and avidin. The method described consists of the hybridization of complementary strands, primer extension reactions, the hybridization of a second biotinylized primer to the primer extension products, and the extension of the second primer. Mention is made of the blotting of copies on a second surface which is coated with avidin.

The disadvantage of the methods referred to above is that multiple replication in the sense of exponential propagation is not possible, and that the translocation of the copies by means of an electromagnetic field cannot be achieved without loss of site information. Based on this state of the art, and avoiding the shortcomings referred to above, it is therefore the task of this invention to provide a method of cloning and copying onto surfaces which permits the propagation of biological material while retaining site information.

SUMMARY OF THE INVENTION

The present invention overcomes the problems and disadvantages of current amplifications methods and enables biological systems including, nucleic acids, ligands and receptors, to be propagated and separated from one another by means of an electric field for immobilization and fixation on one or more solid surfaces, while retaining site information.

The present invention considers a biological system to be basically an interaction between nucleic acids of any kind and/or with peptides/proteins/polymerases/enzymes (DNA/RNA/PNA/pRNA/2'–5' nucleotides and RNA/DNA mirror mers (see PCT/EP97/04726)), in exactly the same way as antigen/antibody complexes or, in general terms, ligand/receptor systems.

For a basic understanding of the invention it is necessary to appreciate that complementary nucleic acids themselves represent nothing more than a special form of a complementary ligand/receptor system in a traditional sense. For purposes of the present application, the term "ligand" will refer to one molecule of the biological binding pair and the term "receptor" will refer to the opposite molecule of the biological binding pair. Two complementary strands of nucleic acid are biological binding pairs. One of the strands is designated the ligand and the other strand is designated the receptor. Biological binding pairs may also comprise antigen and antibodies, drugs and drug receptor sites and enzymes and enzyme substrates.

The invention utilizes the fact that, because of their charge, nucleic acids and many other biologically relevant molecules can be moved within an electrical field when such a field is applied. In the present case a stationary, bound molecule is separated from a corresponding molecule in this way, in that the non-stationary, bound molecule is either separated from the other by synthesization of that molecule or following an "identification reaction", with the aid of an electrical field. Because the molecules tend to migrate along the line of the electrical field, they retain site information while migrating. This is also what mainly distinguishes the method referred to in this invention from the previously known state of the art, because in Federal Republic of Germany Patent No. 694 09 646 T2, for example, site information is not retained, since the electromagnetic field described in that case does not serve to retain the site information.

For all of the alternative processes shown hereinbelow it is possible to alter, reduce and/or increase the (geometrical) scale of the transfer, while retaining site information, within the respective transfer stage of the respective process sequence. This may be practical, for example, if the geometry of the arrays from which or to which the transfer is being made is not identical with that of the initial array or target array.

The present invention in one aspect relates broadly to a method for propagating ligands and receptors on at least two surfaces, comprising:

(a) immobilizing a first ligand on a first surface of a substantially solid phase;

(b) adding a solution of receptors and binding complementary receptors to the first ligand;

(c) transferring the receptor to a second surface and immobilizing the receptor at that location;

(d) attaching an additional ligand to the immobilized receptor; and (e) transferring the additional ligand to the first surface and immobilizing it at that location, wherein the steps set forth above may be repeated multiple times.

Preferably, the surface in step (c) is a second surface which is spatially separated from the first. The additional ligand is transferred to the second surface by the application of an electrical field, and preferably the electrical field is applied between the first and second surface.

Another aspect of the invention relates to enzymatic propagation of a nucleic acid sequence on at least two surfaces, comprising:

(a) immobilizing a first primer on at least one first surface of a substantially solid phase;

(b) administering a solution of nucleic acids comprising complementary fragments to the first primer;

(c) binding of complementary fragments to the first primer;

(d) extending the first primer at its 3' end, corresponding to the complementary fragment by means of a polymerase;

(e) releasing the complementary fragments;

(f) attaching a second primer to the 3' end of the extended nucleic acid;

(g) extending the second primer at its 3' end by means of a polymerase;

(h) transferring the second primer to another surface and immobilization of the extended primer; and (i) attaching another first primer to the 3' end of the second extended primer for further extending of the first primer, wherein the steps of (b) to (h) are repeated numerous times for exponential amplification of nucleic acid sequence.

The second primer as set forth in step (h) is transferred to a second surface which is spatially separated from the first, and the transfer is achieved by the application of an electrical field. Preferably, the electrical field is applied between the first and second surface.

Further amplification stages may occur following the transferal of the second primer to the second surface comprising the following:

(j) extending this first primer to its 3' end, corresponding to the complementary fragment, by means of a polymerase;

(k) transferring of the extended primer to the first or another surface and immobilization of the extended primer thereon; and (l) attaching of another second primer to the 3' end of the extended first primer.

A further aspect of the invention relates to a method for copying nucleic acids from a first to a second surface, comprising:

(a) immobilizing of nucleic acids through a reaction on a carrier surface;

(b) producing a double-stranded molecule by a method selected from the group consisting of hybridization of complementary single strands, chemical or enzymatic ligation of complementary fragments and chemical or enzymatic extension of complementary primers; and (c) transferring of complementary strands to a second surface with immobilization of the complementary strands thereon.

The transfer of the complementary strands to the second surface may be accomplished by the application of an electrical field, in which the electrical field is applied between the first and second surface.

Preferably, the nucleic acids immobilized on the solid carrier are arranged two-dimensionally and are transferred in this order, while retaining site information. The solid phase material is selected from organic or inorganic material or from a hybrid of these materials, and preferably represents a two- or three-dimensional matrix. Immobilization of the nucleic acids and complementary strands occurs through covalent or non-covalent binding.

In still another aspect, the nucleic acids, ligands, receptors or their derivatives are provided with a detectable label. Generally, any molecular moiety capable of detection may be utilized including, by way of example, without limitation radioisotopes, stable isotopes, enzymes, immunoreactive compounds, fluorescence or luminescence chemicals, chromophores, metals or charged particles.

The present invention may be applicable for several different amplification methods including, cloning genomic fragments of DNA, cDNA and RNA, subcloning following restriction-digesting, strengthening an immunological ligand/receptor pair, strengthening the ligand signal, sorting adjacent fragments by using hybridization techniques (chromosome walking), and copying of gene chips.

The term "amplification" is used in the broad sense to mean creating a product which may include, by way of example, additional target molecules, or target-like molecules or molecules complementary to the target molecules, which molecules are created by virtue of the presence of the target molecule in the sample. In a situation where the target is a nucleic acid, an amplification product can be made enzymatically with an agent for polymerization, such as with DNA or RNA polymerases or transcriptases.

The above-discussed embodiments of the present invention will be described further hereinbelow. When the word "invention" is used in this specification, the word "invention" includes "inventions", that is the plural of "invention". By stating "invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DETAILED DESCRIPTION AND PREFERRED EMBODIMENTS

Figure 1A:
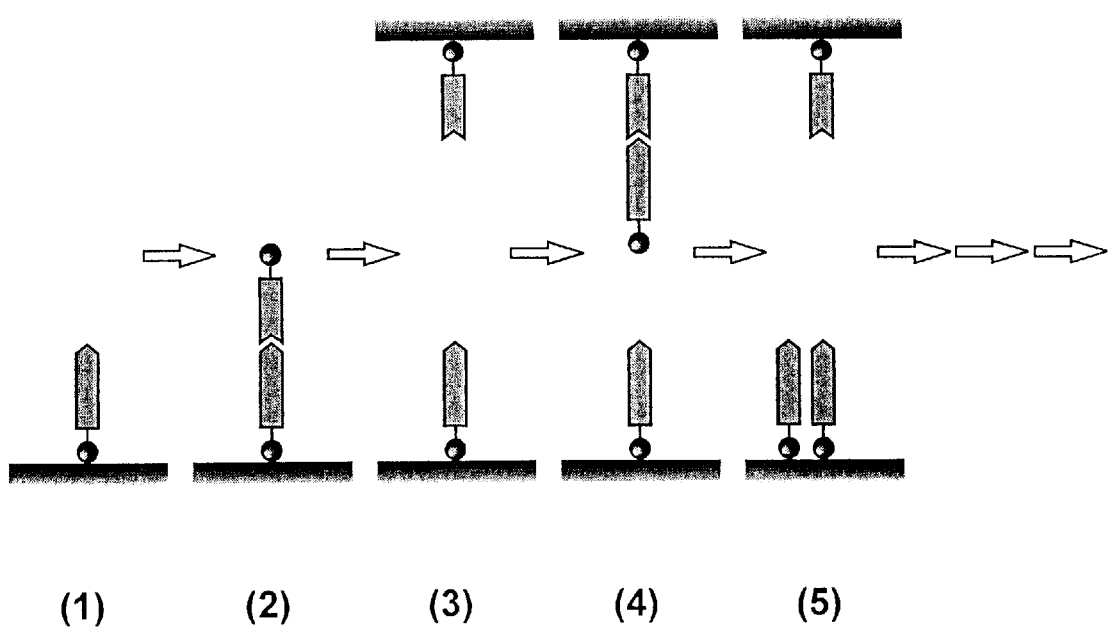
FIG. 1A describes a general process for the propagation of ligands and receptors on two surfaces.

The present invention is a method for cloning and copying ligand/receptor matrices by exponentially amplifying the components of the matrices and immobilizing the components of the matrices on at least one surface and separating the components by means of an electric field while retaining site information.

Nucleotide as used herein means a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. The nucleotides are adenine, thymine, cytosine, guanine and uracil.

Base Pair (bp) as used herein means a partnership of adenine (A) with thymine (T), or of cytosine (C) with guanine (G) in a double stranded DNA molecule. In RNA, uracil (U) is substituted for thymine.

Nucleic acid as used herein means a polymer of nucleotides, either single or double stranded.

Oligonucleotide as used herein makes reference to primers, probes and nucleic acid fragments or segments to be synthesized by ligation of oligonucleotides is defined as a molecule comprised of two or more deoxyribonucleotides or ribonucleotides, preferably at least 5. Its exact size will depend on many factors, which in turn depends on the ultimate conditions of use.

Gene as used herein means a nucleic acid whose nucleotide sequence codes for an RNA or polypeptide. A gene can be either RNA or DNA.

Complementary Nucleotide Sequence as used herein means a sequence of nucleotides in a single-stranded (ss) region of DNA or RNA capable of hybridizing to another single-stranded region for a length of time sufficient to permit the desired reaction, e.g., a ligation reaction or a primer extension reaction.

Conserved as used herein means a nucleotide sequence is conserved with respect to a preselected (reference) sequence if it non-randomly hybridizes to an exact complement of the preselected sequence.

Hybridization as used herein means the pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

The present invention relates to a method of amplification comprising:
  (a) immobilizing a first primer on a first surfaces of a substantially solid phase;
  (b) administering a solution of nucleic acids comprising complementary fragments to the first primer;
  (c) binding of complementary fragments to the first primer;
  (d) extending the first primer at its 3' end, corresponding to the complementary fragment by means of a polymerase;

(e) releasing of the complementary fragments;
(f) attaching a second primer to the 3' end of the extended nucleic acid;
(g) extending the second primer at its 3' end by means of a polymerase;
(h) transferring the second primer to another surface and immobilization of the extended primer thereon; and
(i) attaching another first primer to the 3' end of the second, extended primer.

Specifically, the term "primer" as used herein refers to a molecule comprised of two or more deoxyribonucleotides or ribonucleotides, preferably more than three, which is capable of acting as a point of initiation of synthesis when placed under conditions in which synthesis of a primer extension product which is substantially complementary to a nucleic acid strand is induced, i.e., in the presence of nucleoside triphosphates and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer may be sufficiently long to prime the synthesis of extension products in the presence of the inducing agent for polymerization. The exact lengths of the primers will depend on many factors, including temperature, buffer, nucleotide composition and source of primer. For purposes herein, an oligonucleotide primer typically contains from about 5 to about 50 nucleotides, and preferably from about 5 to about 15.

The primers herein are selected to be "substantially" complementary to each strand of the specific sequence to be amplified. This means that the primers must be sufficiently complementary to hybridize with their respective strands under conditions which allow the agent for polymerization to perform, i.e, the primers have sufficient complementarity with the sequence of the strand to be amplified to hybridize therewith and thereby form a template for synthesis of the extension product of the other primer. Preferably, the primers have exact complementarity with the strand.

The oligonucleotide primers may be prepared using any suitable method. In an automated embodiment, diethylphosphamidites are used as starting materials and may be synthesized as described by Beaucage et al. Tetrahedron Letters (1981), 22:1859–1862. One method for synthesizing oligonucleotides on a modified solid support is described in U.S. Pat. No. 4,458,066. It is also possible to use a primer which as been isolated from a biological source (such as a restriction endonuclease digest).

The role of the solid phase surface (also referred to in the following as a "carrier") in the present invention includes maintaining a separation between the complementary matrices which would form stable duplexes if in solution. Suitable carrier materials consist of organic or inorganic materials or a hybrid of these materials. Organic carrier materials consist of polymers on a sugar basis, preferably agarose, cellulose, and suitable derivatives or technical polymers such as polystyrene, polyacrylate, polyacrylnitril, polyalkene or graft copolymers (e.g. PS PEG, PAN-PEG, PAN-PAG etc.), as well as electrically conductive polymers (e.g. polyvinylpyrrol). Examples of suitable inorganic carrier materials include glass or metals, with particular importance being attached to gold surfaces (as a result of the gold thiolate interaction) and semiconductor surfaces.

A preferred carrier support comprises a sheet that has surfaces with alignment features to allow the precise positioning of the nucleic acids to facilitate the transference of polymerized molecules to another support having the surface defined in the same grid type pattern thereby retaining site location. During the respective transfer stage within the respective method sequence, the scale can be reduced and/or increased, while retaining the site information. The supports may be filters, fibers, membranes, sheets and the like. It is preferable, but not essential, that the surfaces should be arranged so that they are coplanar to one another.

Bonds formed between the primers and support material may be either covalent or non-covalent, with non-covalent bonds encompassing both ionic and non-ionic binding systems, and in particular members of immunological pairs of bonds such as avidin/streptavidin and antigen antibodies. The primers may be immobilized onto the solid support or carrier in any art-recognized way. A commonly used means is to provide a biotin label on the primer for binding to a streptavidin-coated support. Suitable binding linkers should not form undesirable interactions with other factors occurring in the system. In particular, in the hybridization of a primer, no interaction with surface zones containing the template should occur. This imposes the requirement for a controllable binding chemistry that can be influenced by external conditions.

Faulty immobilization can be prevented by using pairs of primers (see below) instead of an "activatable reactive primer". It should be possible to immobilize the extension products of these pairs of primers orthogonally. In this case orthogonally means that no binding points are available for a primer that is hybridized on a template, but that binding points are available following translocation of the primer extension product to the opposite surface. The way in which the primer is added, and the way in which the reaction is allowed to take place must take this aspect into account. As defined by this invention, activatable reactive primers are considered to be those primers that function reactively and whose reactivity can be influenced by the choice of suitable external conditions.

Any source of nucleic acid, in purified or non-purified form, can be utilized as the starting nucleic acid or acids, provided it contains or is suspected of containing the specific nucleic acid sequence associated with that to be detected and amplified. One may select the sequence being amplified from among the regions that are substantially conserved among the biological material of interest. The method of the present invention may employ, for example, DNA or RNA, including messenger RNA, and the DNA or RNA may be single stranded or double stranded. In the event that RNA is to be used as a template, enzymes and/or conditions optimal for reverse transcribing the template to DNA should be utilized. In addition, a DNA-RNA hybrid which contains one strand of each may be utilized. A mixture of any of these nucleic acids may also be employed, or the nucleic acids produced from a previous amplification reaction herein using the same or different primers may be so utilized.

The target nucleic acid sequence to be amplified or copied may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the virus-encoding gene contained in a whole human DNA. The starting target nucleic acid may contain more than one desired specific nucleic acid sequence which may be the same or different. Therefore, the present method is useful not only for producing large amounts of one specific nucleic acid sequence, but also for amplifying simultaneously more than one different specific nucleic acid sequence located on the same or different nucleic acid molecules.

In the process described herein, the copies of nucleic acids thus produced may be identical or complementary to the initial sequence (matrix). "Complementary" in the case of this invention is taken to mean that the copy of the matrix differs from the initial matrix, whereas the copy of this copy is identical with the initial matrix. If necessary, these will be referred to in abbreviated form in the following as the "(+) strand" and "(−) strand". The reactions take place in the same reaction vessel. Nucleic acids are taken to mean both D- and L-nucleic acids (mirror mers), and any kind of modifications to them.

The nucleic acid(s) may be obtained from any source, for example, natural DNA or RNA from higher organisms such as animals. DNA or RNA may be extracted from a bodily sample such as blood, tissue material such as chorionic villi, or amniotic cells by a variety of techniques such as that described by Maniatis et al., Molecular Cloning (1982), 280–281. Preferably, the first nucleic acid has a size of approximately 1 to 10 Kb. Larger nucleic acid can be readily digested by enzymes or mechanically fragmented.

Any specific nucleic acid sequence can be copied and amplified by the methods of present invention. It is only necessary that a sufficient number of bases at both ends of the sequence be known in sufficient detail so that at least one oligonucleotide primer can be prepared that will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be substantially conserved with the end of the desired sequence to be amplified.

A nucleic acid sequence is produced by using the target nucleic acid containing that sequence as a template. If the target nucleic acid sequence of the sample contains two strands, it is necessary to separate the strands of the nucleic acid before it can be used as the template. This strand separation can be accomplished using any suitable denaturing conditions, including physical, chemical or enzymatic means, the word "denaturing" used herein to include all such means. One physical method of separating the strands of the nucleic acid involves heating the nucleic acid until it is denatured. Typical heat denaturation may involve temperatures ranging from about 80° C. to about 105° C., for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, CSH-Quantitative Biology, 43:63 (1978), and techniques for using RecA are reviewed by C. Radding, Ann. Rev. Genetics, 16:405–37 (1982).

If an appropriate primer is immobilized on a support surface and a single-stranded target nucleic acid sequence (acting as a template) is added to a system then a primer extension product is synthesized in the presence of a polymerization agent, and the four nucleoside triphosphates described below. The product will be at least partially complementary to the single-stranded target nucleic acid and will hybridize with the target nucleic acid strand to form a duplex of substantially equal length strands that may then be separated into single strands as described above to produce two single separated complementary strands.

The techniques used for amplifying and thereafter detecting the product are described in detail U.S. Pat. Nos. 4,683,195 and 4,683,202, the entire disclosures of which are incorporated herein by reference. In general, the amplification process involves an enzymatic chain reaction for preparing, in exponential quantities relative to the number of reaction steps involved, a specific nucleic acid sequence, given that the ends of the required sequence are known in sufficient detail that oligonucleotide primers can be synthesized which will hybridize to them, and that a small amount of the sequence is available to initiate the chain reaction. Preferably, one primer is complementary to the negative (−) strand and the other is complementary to the positive (+) strand.

The synthesis is performed under conditions allowing hybridization of primers to templates to occur. Generally, hybridization occurs in a buffered aqueous solution, preferably. at a pH of about 7 to about 9, most preferably about 8. Preferably, a molar excess of the primers is added to a buffer solution for immobilization on the support before the template strands are introduced. It is understood, however, that the amount of template strand may not be known if the process herein is used for diagnostic applications, so that the amount of primer relative to the amount of template (complementary) strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Deoxyribonucleoside triphosphates dATP, dCTP, dGTP and dTTP are also added to the synthesis mixture in adequate amounts to provide sufficient building blocks for synthesizing an extended primer sequence and the resulting solution is heated to about 90° C. to about 110° C. for about 1 to 15 minutes, preferably from 1 to 4 minutes. After this heating period the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis reaction may occur at from room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation), that will facilitate combination of the nucleotides in the proper manner to form the primer extension products which are complementary to each nucleic acid strand used as a template. Generally, the synthesis will be initiated at the 3' end of each primer and proceed in the 5' direction along the template strand, until synthesis terminates. There may be agents for polymerization, however, which initiate synthesis at the 5' end and proceed in the other direction, using the same process as described above.

The newly synthesized strand and its complementary nucleic acid strand (template strand) will form a double-stranded molecule under the hybridizing conditions described above and this hybrid is used in the succeeding steps of the process. In the next step, the double-stranded molecule is subjected to denaturing conditions using any of the procedures described above to provide single-stranded molecules if the target sequence is present. Denaturation of the complementary strands can be performed by subjecting the system to heat, for example 90° C. to 110° C. for about 2 to 15 minutes, or highly alkaline conditions, such as by the addition of sodium hydroxide. Denaturation can also be accomplished by adding organic acids, nucleic acid binding proteins or enzymes which promote denaturation.

Preferably, the release of the first nucleic acid (template strand) allows further amplification of the desired product by allowing the extended nucleic acid sequence to act as a template for further hybridization reactions to form a second hybridization product. New nucleic acid may be synthesized on the single-stranded first hybridization product which is the extended nucleic acid sequence. Additional agent for polymerization, nucleotides and primers are added, if necessary, for the reaction to proceed under the conditions prescribed above. Preferably a second primer is attached to the 3' end of the extended nucleic acid sequence and the second hybridization product will mimic the sequence of the first nucleic acid template strand. The 5' end of the second primer, attaches to the first extended nucleic acid, so that the 3' end of the primer can be extended in the next hybridization process. The second primer will include a functional 5' end group to facilitate immobilization on a second solid support in subsequent reactions.

Upon completion of the second hybridization product, the double stranded nucleic acid molecules comprising the first and second extended nucleic acid sequences is separated by any denaturing process as discussed hereinabove. Upon separation of the double stranded nucleic acid molecules, the first solid phase support is introduced to a standard electrophoresis chamber comprising a second solid phase surface. Application of an electric field, in the electrophoresis chamber causes the newly hybridized nucleic acid strands (after separation) to migrate towards the second solid phase surface for an immobilization reaction.

The present inventive method for amplifying target sequences comprises subjecting the synthesized nucleic acid strands in a suitable medium to an electric field generated by at least two electrodes arranged which serve as driving electrodes. A standard horizontal gel apparatus is described in T. Maniatis, E. F. Fritsch, and J. Sambrook, Molecular Cloning: A Laboratory Manual, 153 (Cold Spring Harbor Laboratory, 1982) which comprises a positive and negative electrode, submerged in solution at opposite ends of a buffer tank.

The driving electrodes have a potential difference imposed across them and this determines the general direction of the electric field. The electric field effectively controls the migration of the non-immobilized strand of nucleic acid effecting separation of nucleic acids strands. The field may be uniform or non-uniform and alternating/non-alternating fields may also be employed for modifying the resolution, migration path and rate of separation.

The electrophoresis is carried out in a gel conventionally prepared using agarose or polyacrylamide as the gelling agent, although other gelling agents may find use. In carrying out the method of the subject invention an electric field of a desired shape is created in the gel. The field is maintained during the electrophoresis and may be uniform or non-uniform, alternating or non-alternating. The gel is supported in a reservoir containing a buffered medium and located between the electrodes. The solid phase support may be loaded near one end of the gel. The gel is positioned within the electrode array to provide the proper migration direction for the charged sequence.

In practice, the electrodes are suspended in a buffer tank and immersed in a buffer solution. The buffer solution can be circulated and cooled in conventional fashion. The first solid phase support is positioned in the chamber so that the direction of travel of the free nucleic acid is towards the second solid phase support. The potential across the electrodes is determined by the size of the free nucleic acid sequence that are moved through the electric field. The velocity of the free nucleic acids or biological materials is dependent on the strength electric field, the net charge on the free nucleic acid and friction resistance. The isoelectrical point should be determined for the free nucleic acid to determine the appropriate pH in the solution for increased velocity because the net charge is dependent upon the pH of the solution. Further, the primers may be provided with charged groups to increase the velocity in the electric field. The electric field may be continuous or pulsed and pulse times and voltages will vary with the size of the molecules to be resolved, pulse times being longer with larger biological molecules. Pulse times will generally be in the range of 1 second to several hours, more usually in the range of 5 seconds to 60 minutes. The voltages will generally be in the range of about 50 to about 500 volts which will effectively cause the migration of the free nucleic acid sequence in the direction of the second solid phase surface.

Upon contact of the second primer with the second solid phase surface, it is immobilized thereon by attaching of the 5' end of the second primer with a functional grouping on the second solid phase surface.

The steps of extension product synthesis, denaturing and application of an electric field can be repeated as often as needed to amplify the first target nucleic acid sequence to the extent necessary for detection. The amount of the synthesized nucleic acid sequence produced will accumulate in an exponential fashion.

When it is desired to produce more than one synthesized extended nucleic acid sequence from a mixture of target nucleic acids, the appropriate number of different oligonucleotide primers are utilized. For example, if two different nucleic acid sequences are to be synthesized, four primers are utilized. Two of the primers are specific for one of the specific nucleic acid sequences and the other two primers are specific for the second nucleic acid sequence. In this manner, each of the two different sequences can be produced exponentially by the present process.

The invention also applies in particular to a process for the enzymatic propagation of nucleic acids on at least two surfaces, and incorporating one or more of the following amplification cycles (a) immobilizing a first primer on a first surface of a solid phase;

(b) adding a solution of nucleic acids and binding of complementary fragments to the first primer;

(c) extending the first primer at its 3' end, corresponding to the complementary fragment, by means of a polymerase;

(d) releasing the complementary fragments by denaturing;

(e) adding a second primer to the 3' end of the extended nucleic acid;

(f) extending the second primer at its 3' end by means of a polymerase;

(g) releasing the second primer extended nucleic acid and transferring to an additional surface for immobilization thereon;

(h) adding additional first primer for extending the additional first primer to the 3' end of the second extended primer.

The present method is useful for the propagation of biological material on so-called "gene chips". Basically it is immaterial (as it is in any case in the method involved in this invention) whether the 5' end, the 3' end or an internal position within the sequence is used as the starting point for the link with the surface.

The knowledge already exists regarding the attachment or synthesis of a large number of immobilized polymer compounds onto an object carrier as a way of demonstrating the action of selectively binding compounds on such carriers (Fodor et al., Science 251, 767–773, 1991; U.S. Pat. Nos. 5,510,270, 5,489,678, 5,445,934, and 5,424,186). However, the process of producing such arrays of probes must be preceded by the creation and use of lithographic masks, and the initial monomer compounds must be provided with light-sensitive protective groups. The synthesis cycle in the case of peptide synthesis requires at least 20 such masks for each cycle, i.e. for n cycles the number of masks required is n×20; in the synthesis of oligonucleotides 4 such lithographic masks are required, i.e. if there are n cycles, n×4 masks are required. These lithographic masks are needed to permit illumination at defined spatial points on the array, while preventing illumination at other points on the array. A light-sensitive protective group is split off at the defined, illuminated points, and this enables a reactive group to be released, to which a new monomer building block of the polymer can subsequently bind. Such arrays are built up through the repeated application of individual masks and the multiple repetition of coupling processes. Until now complicated and extremely expensive lithographic methods have been needed to produce such gene chips (see also U.S. Pat. No. 5,700,637).

The methods of the present invention unexpectedly provide a simple alternative to such methods described in the prior art, and moreover offer much greater levels of efficiency and precision. Because of the wealth of information that can be held on such gene chips, it is even possible to prepare entire genetic databases or libraries for screening purposes. The purpose of this invention is to arrange the nucleic acids two-dimensionally on the fixed carrier, and to transfer them in accordance with this arrangement. As defined by this invention the two-dimensional arrangement can also be regarded as a "disarray". Especially in the case of large libraries there inevitably no specific allocation with regard to the way in which individual molecules bind to particular sites. In a spatial sense, however, when a transfer takes place the non-allocated molecules of the library are transferred along with their original, site-specific information. We then have a "disarray" which, at the same time, is transferred in an organized form, while retaining site-specific information.

Additional applications for the present invention include the production of gene chips for diagnostic purposes in both human and veterinary medicine.

Immune reactions in the form of immunoassays or RIAs (antibody-antigen reactions) can also be carried out using the methods referred to in this invention.

The invention offers previously unsuspected advantages for all known, relevant methods, i.e. conventional, medico-diagnostic and biochemical/biotechnological/genetic engineering, and consequently it opens up many fields of application. A few of these applications are set forth below.

The method referred to in this invention can be used for the qualitative and quantitative detection of DNA and RNA molecules. This method also enables complex genetic polymorphism and multiple alleles to be analyzed simultaneously. The propagation of the DNA or RNA molecules on solid phases enables the avoidance of primer artifacts (e.g. primer-dimers). The fact that the sample to be quantified is only introduced at the start of the process and that subsequently all propagation products are firmly attached to the surfaces by specific bonds can be seen as yet another advantage. In this way the frequent interference from signals produced by impurities during PCR diagnosis is avoided. Surface purity can be improved by the electrostatic rejection of non-specifically bonded DNA or RNA molecules. The method can therefore be applied in functional genomics and pharmacogenomics (see Oliver et al. Trans Biotechnol. 16, 373–378 (1998); Housman and Ledley, Nature Biotechnology 16, 492–493 (1998)).

The methods referred to in this invention can be used to detect differential gene expressions. Furthermore the process can be combined with state of the art methods such as differential display RT-PCR (DDRT-PCR), serial analysis of gene expression (SAGE) or differential hybridization (Wan et al., Nature Biotechnology 14, 1685–1691 (1996)).

For rapid qualitative and quantitative detection the methods of the present invention can be combined with known, state-of-the-art sensoring methods, e.g. surface plasmon resonance sensors, evanescent field sensors, faser optic sensors, grating couplers or RIFS (reflector-interferometer spectroscopy) (Scheller et al., Frontiers in Biosensorics, Birkhäuser Verlag Basel (1997)).

The compilation of gene and genome libraries in accordance with this invention can be combined with the known, state of the art process for the ligation of adapters or linkers. One particular advantage of this process is that, when two different primers are used for surface immobilization, only molecules with two different adapters or linkers are propagated. In this way the respective, complementary, individual strands on the surfaces are propagated separately.

Moreover, a combination is also possible with processes which permit site-specific immobilization and the re-sorting of surface-bonded molecules. These include firstly the methods based on arrays of electrodes in which one or more specific microelectrodes can be selectively triggered. In such cases, the arrays of electrodes may be made up using semiconductor chips, for example, such as those developed by the Nanogen Company (www.nanogen.com). Other methods involve the use of scanning techniques, in which piezoelectric elements are used to ensure extremely precise lateral addressing down to the sub-nanometer range. The preferred approach involves the use of scanning electrochemical microscopy (SECM) for electrochemical deposition of molecules. This can also be used in association with electrochemical probes for detection purposes. Methods such as atomic force microscopy (AFM) are also suitable for the lateral translocation of individual molecules.

The gene and genome libraries compiled in accordance with the methods of the present invention can be sequenced using the known state-of-the-art method, e.g. sequencing by chemical splitting, sequencing by hybridization, sequencing by capillary electrophoresis or MALDI mass spectrometry (see Adams, Fields, Venter in: Automated DNA Sequencing and Analysis, Academic Press, 1994). The gene and genome libraries thus compiled can be used to allocate DNA and RNA-binding factors. For example the specific binding sites for transcription activators or repressors can be detected simultaneously. The gene and genome libraries used may be either single or double stranded.

The methods of the present invention may be used for gene and genome synthesis and for the recombination of genetic material. The method described in FIG. 7 (see below) permits the connection of any number of fragments possessing only partial complementarity. In particular it enables open scanning grids to be provided with suitable starting signals for biological expression systems. In addition the process can be coupled with in-vitro transcription and in-vitro translation, because transcription and translation products can be created while retaining site information. Also, it is possible to test the spatial arrangement of these products in the way that they interact with other factors. This enables functional allocations to be detected simultaneously which, in the current state of the art, is only found in complicated systems such as the "Two Hybrid-System" (Fredericson, Curr. Opin. Biotechnol. 9, 90–96 (1998)). Thus, using the present methods, new effective pharmacological sites can be found, or new diagnostic strategies developed.

Moreover, the process can be combined with known, state of the art methods for finding functional molecules from combinatorial libraries. For example, a target molecule can be immobilized on a first surface. The non-binding RNA or DNA molecules can be separated following contact with a combinatorial nucleic acid library. The binding molecules obtained from the combinatorial library are transferred to a second surface, using the process to which this invention refers. They are provided with information about the site and then propagated. Details about the composition of the binding molecules can be obtained through sequencing.

In addition a cyclical procedure can be used to achieve evolutive optimization of the binding molecules. The molecules that have already been selected are again brought into contact with the immobilized target molecules and are again propagated. Faulty propagation leads to the creation of secondary molecules, in some cases with improved binding properties. The population of the sequence derived from the primary sequence through mutation is referred to by Eigen as a quasi-sequence. The process to which this invention refers is distinguished by the fact that the members of the quasi-species are spatially co-localized, giving a lateral dimension to the concept of the quasi-species.

By applying increasingly stringent conditions, e.g. reduction of the target concentration and increased flushing, it is possible to attain systematic optimization of the functional properties. The selection pressure can also be achieved through increasing electrostatic repulsion. Moreover the process can also be combined with known, state of the art methods for the selection of catalytic nucleic acids (Tarosow et al., Nature 389, 54–57 (1997)).

Consequently, the methods of the present invention can be used in particular for cloning genomic fragments of DNA, cDNA and RNA, especially using replicative polymerases, e.g. polymerase III derived from *Escherichia coli*. Advantageously, errors are avoided in the replication process. Moreover, subcloning is available following restriction-digesting. Subcloning has a part to play in the sequencing of large genomic fragments and the present methods achieve considerable time savings during sorting the large libraries of nucleic acids, for example by the use of subcloning techniques such as "shotgun cloning" and the creation of selective deletion variants, e.g. exonuclease III treatment (see Adams, Fields, Venter, in: Automated DNA Sequencing and Analysis, Academic Press, 1994).

Further, the present invention has advantages for sorting adjacent fragments through the use of hybridization techniques ("chromosome walking").

Using the instant methods in order to copy gene chips offers previously unsuspected possibilities. For example, gene chips can be used with a library of viral antigens as the source material. The reaction with a patient's blood and the action of binding the antibodies that the blood contains enable an immune reaction to be detected. The process can be repeated any number of times, which in turn strengthens the signal. To an extent a linear propagation thus takes place, weak immune signals can be identified. This is useful, for example, in the diagnosis of AIDS, which, as is commonly known, is difficult to detect at the start of the infection. It is also possible to identify diseases or allergies in their early stages. The present methods are also suitable for the exponential propagation which may occur when using an immobilized antigen. In addition, using semi-conductor technology and/or micromanipulation ("align techniques") a sorting process can be carried out on gene chips. It is also possible to provide the charged nucleic acids with a positively charged group of headings, which predominates in the overall charge. This enables the molecules to be aligned in the electrical field, permitting a high charge density on the chips (DNA/RNA).

FIG. 1A describes a general process for the propagation of ligands and receptors on two surfaces; the individual stages are:

(1) as a result of a binding reaction, a ligand is immobilized on the surface of a solid carrier;

(2) the ligand binds a receptor;

(3) the receptor is transferred to a second surface by the application of an electrical field whereon the receptor is immobilized by a reaction;

(4) a free ligand is added to the immobilized receptor; and (5) the ligand is transferred to the second surface (with the aid of an electrical field) for immobilization thereon.

The process may be carried out or repeated any number of times.

Figure 1B:
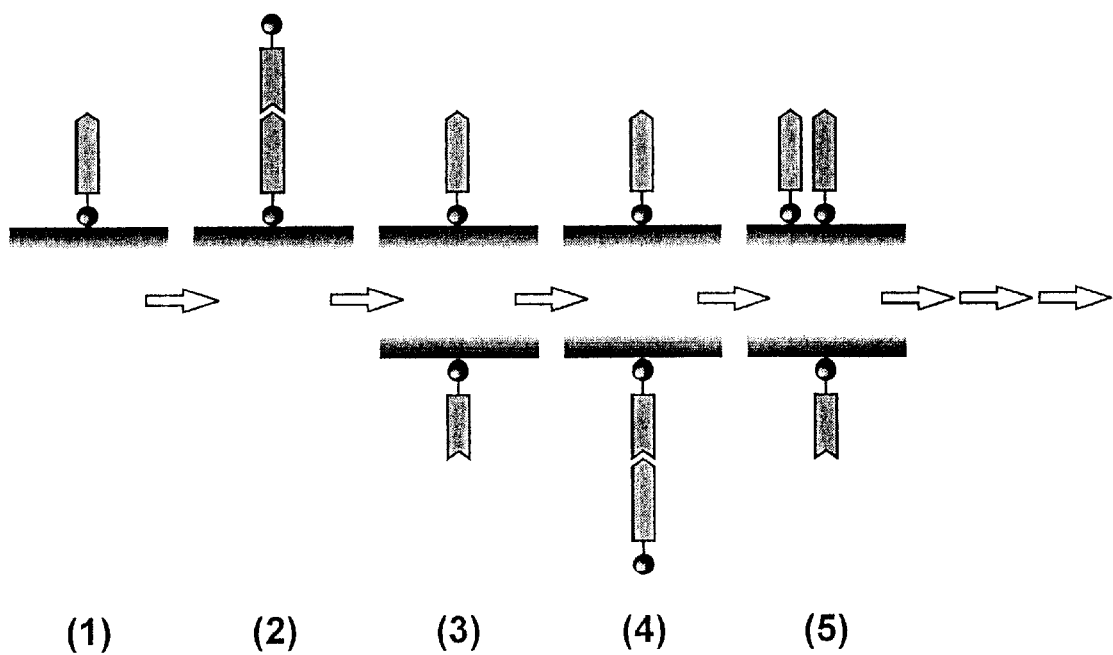
FIG. 1B shows the process in accordance with FIG. 1, having an intermediate layer placed between the two surfaces.

FIG. 1B shows the process in accordance with FIG. 1A, but here an intermediate layer is placed between the two substantially solid phase surfaces. This intermediate layer is chosen from among a group comprising a gel, a membrane, a polymer, a ceramic and/or a so-called capillary tube array. When an electrical field is applied, the non-immobilized molecule travels via the intermediate layer to the second surface, where it is immobilized. The intermediate layer can be permeated by nucleic acids and/or ligands/receptors.

Figure 2:
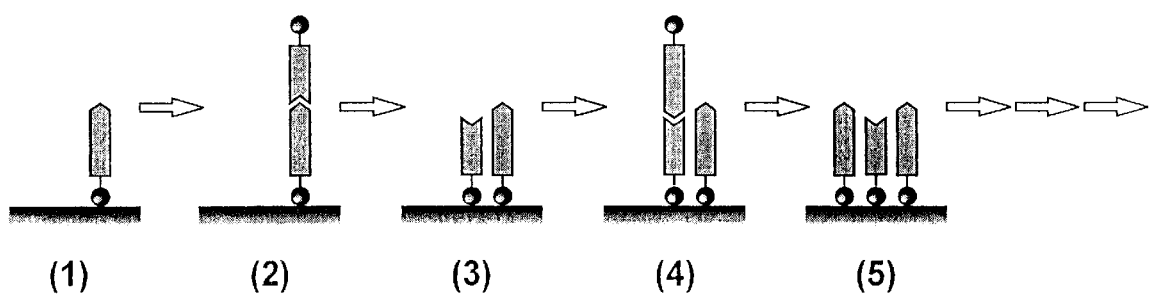
FIG. 2 describes a general process for propagating ligands and receptors on a surface.

FIG. 2 describes a general process for propagating ligands and receptors on a surface; the individual stages are:

(1) a ligand is immobilized on the surface of a solid carrier by a binding reaction;

(2) the ligand binds a receptor;

(3) the receptor is transferred to the surface by the application of an electrical field to be immobilized thereon by a reaction;

(4) a free ligand is added to the immobilized receptor; and (5) the ligand is immobilized on a surface by means of a reaction.

The process may be repeated any number of times.

Figure 3A:
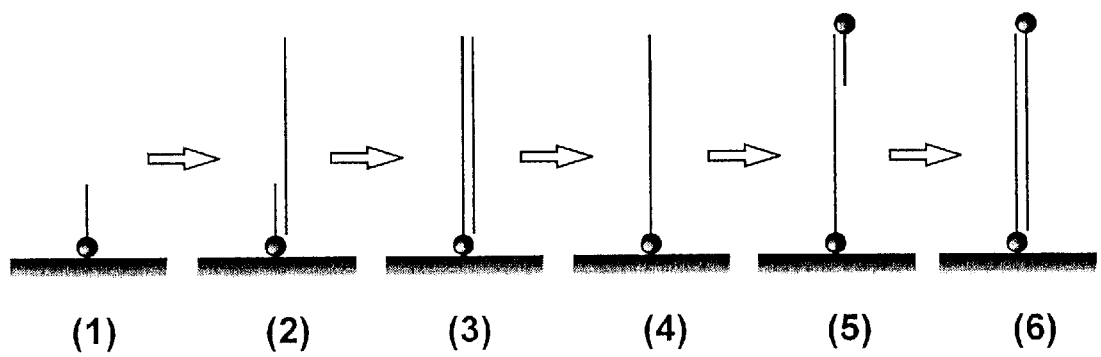
FIG. 3A describes a process for the enzymatic propagation of nucleic acids on two surfaces.

FIG. 3A describes a process for the enzymatic propagation of nucleic acids on two surfaces, with the individual stages of the process being shown in fast motion as follows:

(1) a first primer A is immobilized by a binding reaction on a solid carrier surface;

(2) the primer A bonds complementary fragments from a solution of nucleic acids;

(3) the primer A is extended by a polymerase at its 3' end;

(4) the complementary fragments are released;

(5) a second primer B is added to the 3' end of the extended nucleic acid;

(6) the primer B is extended by a polymerase at its 3' end;

(7) the extended, non-immobilized primer B is transferred to a second surface by applying an electrical field, wherein the two surfaces having opposed polarities, and the extended primer B is immobilized thereon by a binding reaction;

(8) an additional primer A is added to the 3' end of the extended primer B;

(9) the primer A is extended by a polymerase at its 3' end;

(10) the extended primer A is transferred to an additional surface by applying an electrical field, with the two surfaces having opposed polarities, and the extended primer A is immobilized there by a reaction; (in this case, unlike in stage (7) the polarities are reversed) (11) another primer B is added to the 3' end of the extended primer A.

The process is then repeated any number of times, preferably by means of a cycle of polarity reversals.

Figure 3A:
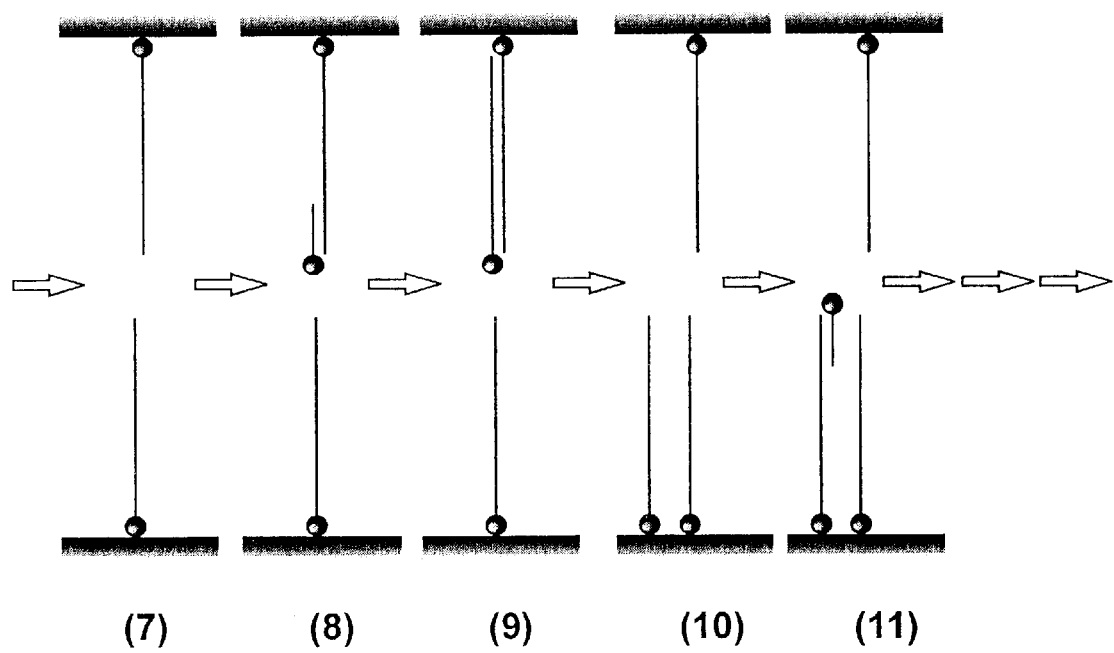
Figure 3B:
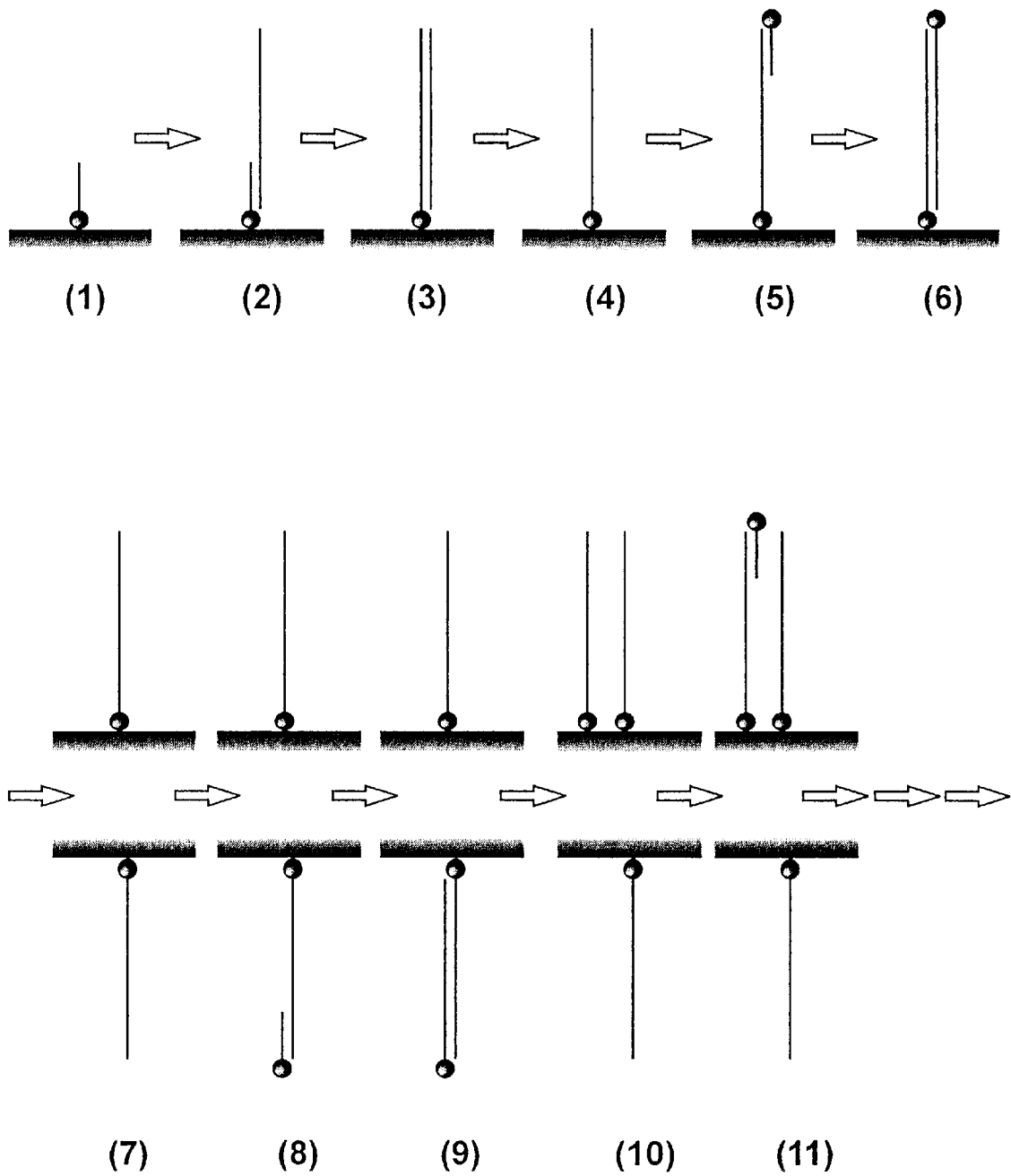
FIG. 3B shows the process in accordance with FIG. 3, having an intermediate layer placed between the two surfaces.

FIG. 3B shows the process in accordance with FIG. 3A, but here an intermediate layer is placed between the two surfaces. This intermediate layer is chosen from among a group comprising a gel, a membrane, a polymer, a ceramic and/or a so-called capillary tube array. When an electrical field is applied, the non-immobilized molecule travels via the intermediate layer to the second surface, where it is immobilized.

Figure 4:
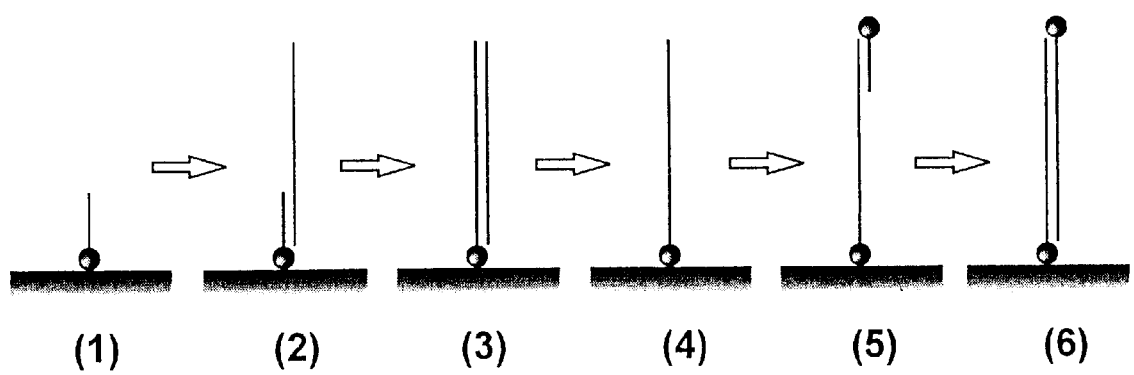
FIG. 4 shows a basic process for the enzymatic propagation of nucleic acids on only one surface.
Figure 4:
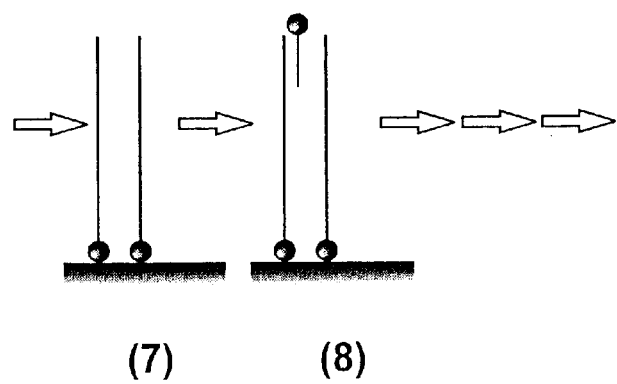

FIG. 4 shows a basic process for the enzymatic propagation of nucleic acids on only one surface; the individual stages are as follows:

(1) a first primer A is immobilized by a reaction on the surface of a solid carrier;

(2) the primer A binds complementary fragments from a solution of nucleic acids;

(3) the primer A is extended by a polymerase at its 3' end;

(4) the complementary fragments are released;

(5) a second primer B is added to the 3' end of the extended nucleic acid;

(6) the primer B is extended by a polymerase at its 3' end;

(7) the extended, non-immobilized primer B is transferred to the surface of the solid carrier by applying an electric field and bonded thereon by means of an irreversible reaction, the charged primer B being conducted along the field; and (8) an additional primer A is added to the 3' end of the extended primer B.

The process can be continued any number of times.

Figure 5:
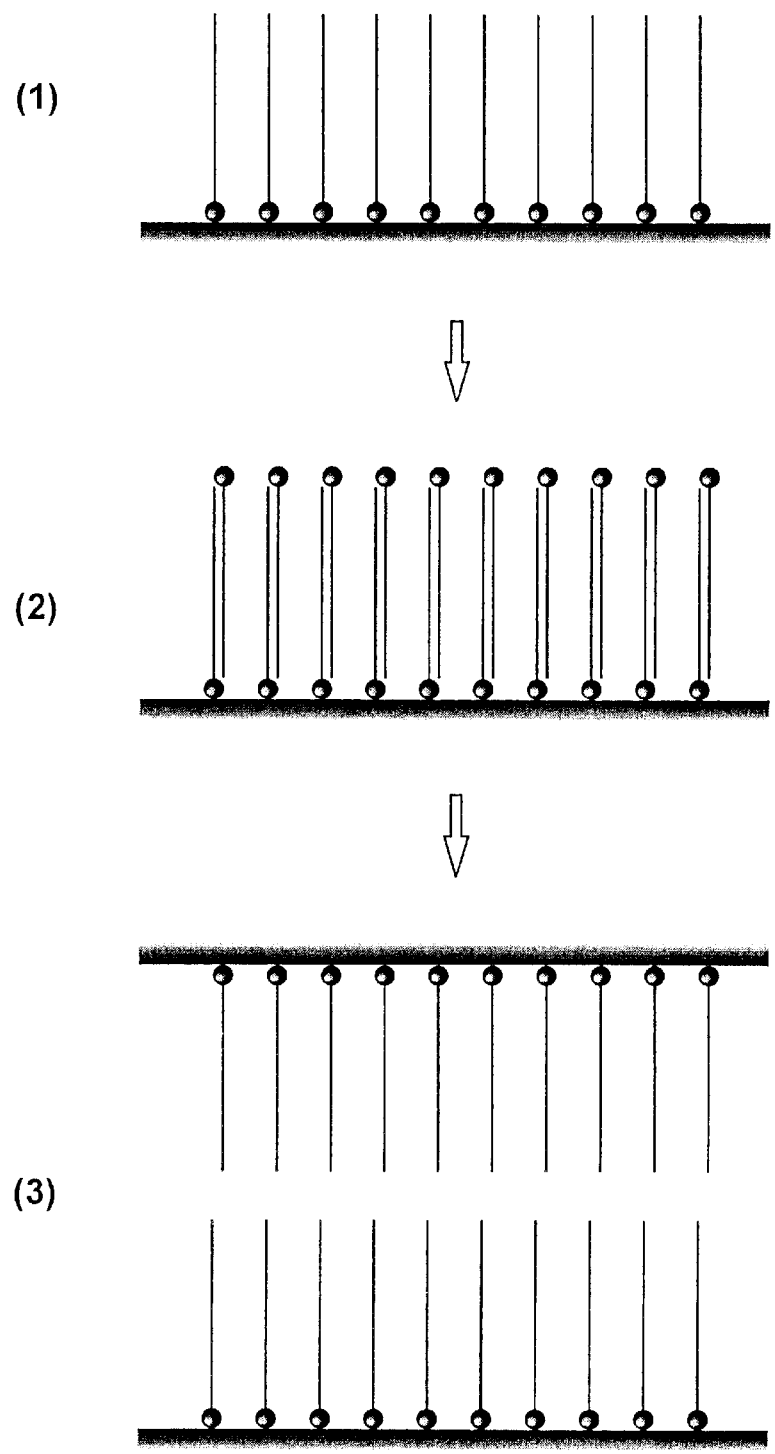
FIG. 5 shows a process for copying nucleic acids onto a second surface.

In contrast, FIG. 5 shows a process for copying nucleic acids onto a second surface; the individual stages are as follows:

(1) immobilization of nucleic acids by a reaction with the surface of a solid carrier;

(2) production of double-stranded molecules through the hybridization of complementary single strands; alternatively chemical or enzymatic ligation of complementary fragments may take place, or chemical or enzymatic extension of complementary primers; and (3) transfer of complementary strands to a second surface, where they are immobilized; this is done preferably by applying an electrical field, the two surfaces being of opposing polarities.

Figure 6:
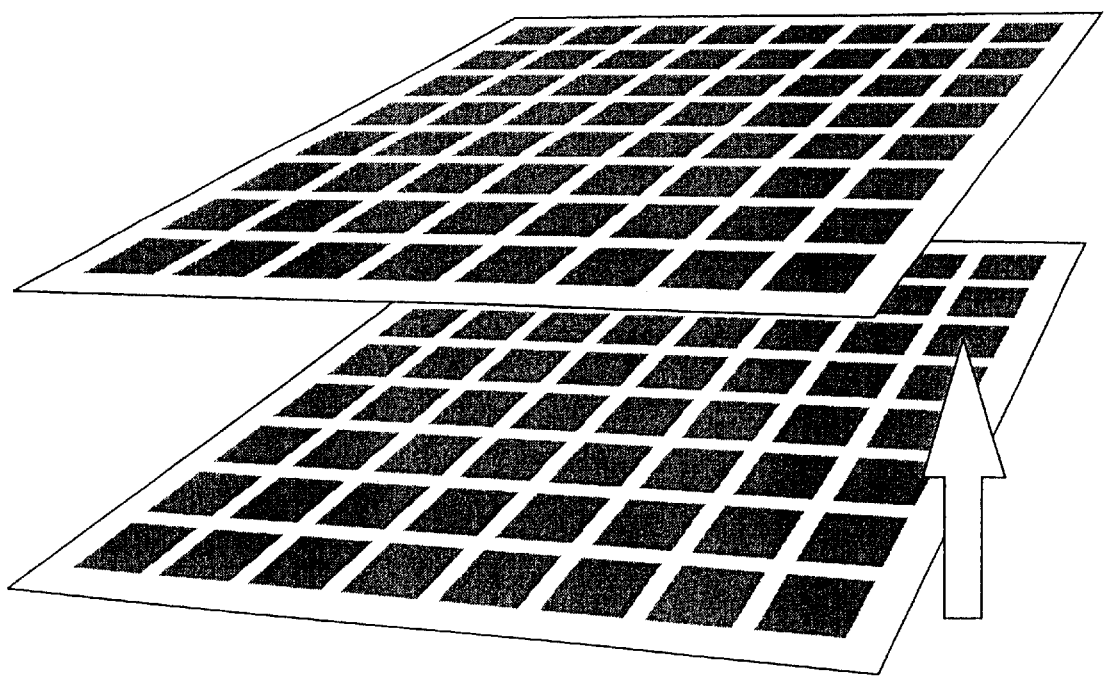
FIG. 6 is a diagram showing two systems coordinates containing numerous fields which are intended to illustrate two surfaces.

FIG. 6 is a diagram showing two systems of coordinates containing numerous fields which are intended to illustrate two surfaces, such as those used, for example, in the case of gene chips or membranes. The lower surface contains the information to be copied, which is transferred to the upper surface by the application of an electrical field (not shown) corresponding to the process described in FIG. 3A. It is then immobilized on this surface.

Figure 7:
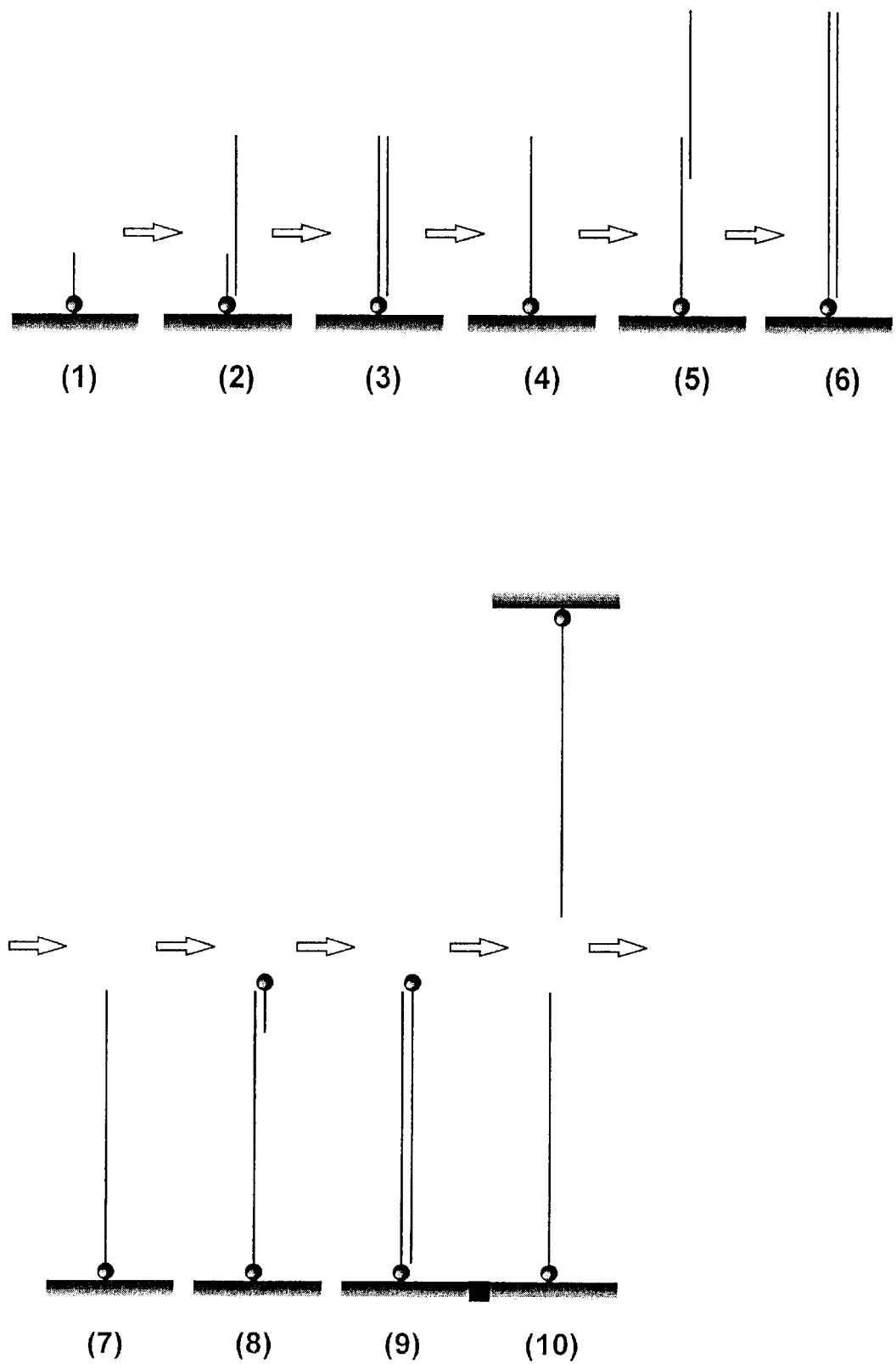
FIG. 7 shows a process for synthesizing genes and genomes, and for recombination.

FIG. 7 shows a process for synthesizing genes and genomes, and for recombination; the individual stages are as follows:

(1) a primer A is immobilized by a reaction on the surface o of a solid carrier;

(2) the primer A binds complementary fragments from a solution of nucleic acids;

(3) the primer A is extended by a polymerase at its 3' end;

(4) the complementary fragments are released;

(5) a second fragment, complementary with the 3' end of the extended primer A, is added, and here partially complementary fragments with overhanging 3' ends are sufficient;

(6) the extended primer A is elongated;

(7) the complementary fragments are released.

Stages (5)–(7) can be repeated any number of times;

(8) a second primer B is added at the 3' end of the extended primer A;

(9) the primer B is extended by a polymerase at its 3' end; and

(10) as described in FIG. 1A, Stage 7, the extended primer B is transferred to a second surface. The advantage of this step is that incompletely extended primer A molecules are separated out. The extended primer B can again be used for extension reactions.

Figure 8:
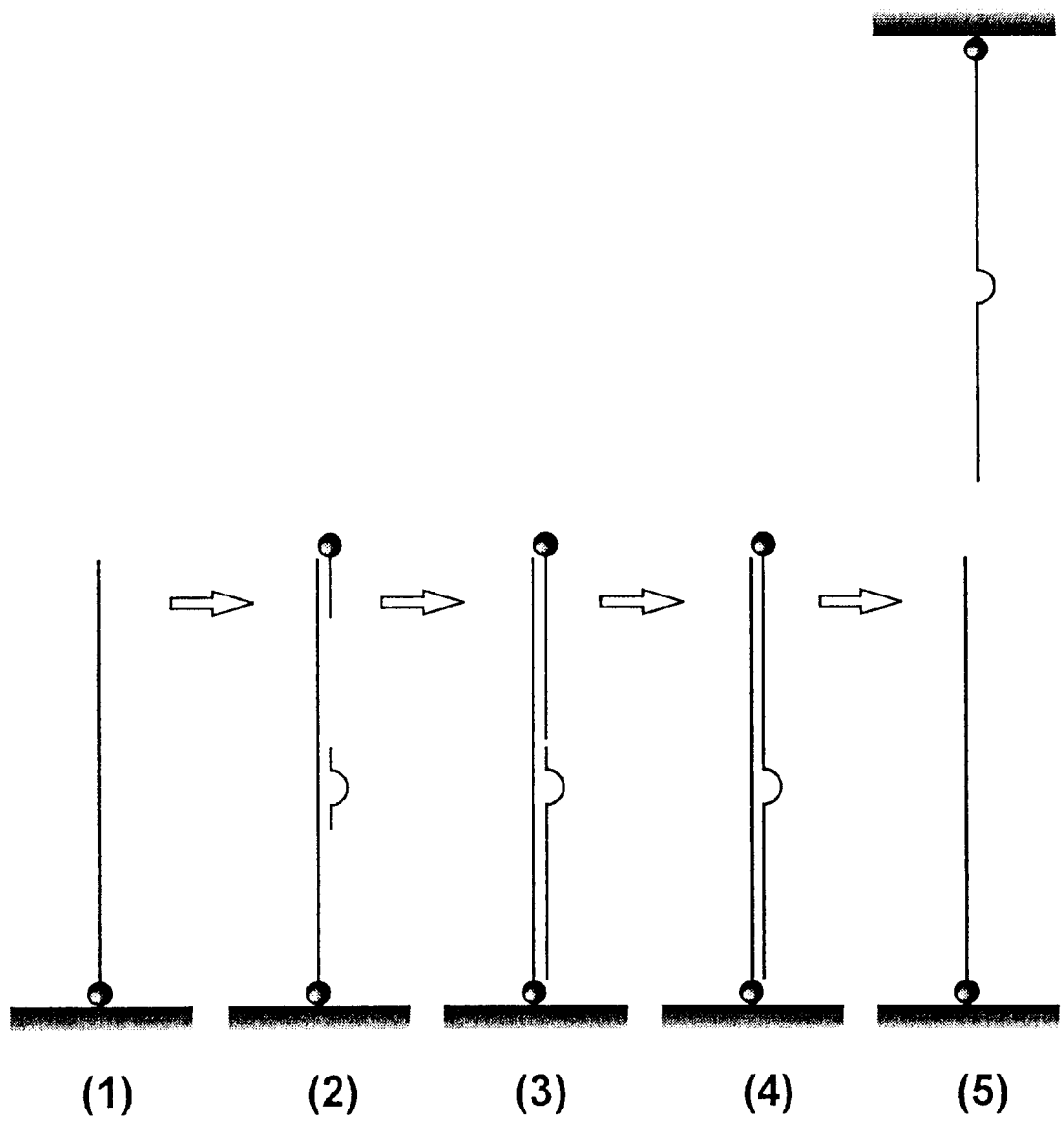
FIG. 8 shows a process for the selective mutagenesis of nucleic acids site-directed mutagenesis.

FIG. 8 shows a process for the selective mutagenesis of nucleic acids (site-directed mutagenesis); the individual stages are as follows:

(1) a nucleic acid A immobilized by a reaction on the surface of a solid carrier; the nucleic acid may be one of the products of the processes referred to above;

(2) the nucleic acid A binds complementary fragments from a solution of nucleic acids which display defective base pairing (mutation fragment); a primer B is also added; the mutation fragment may also be identical with the primer B;

(3) the mutation fragment and the primer B are extended;

(4) the extended molecules are ligated with one another; and (5) the extended primer B is transferred to a second surface, as described in FIG. 1A, Stage 7.

The advantage of this approach is that the second surface only contains mutated molecules.

Figure 9:
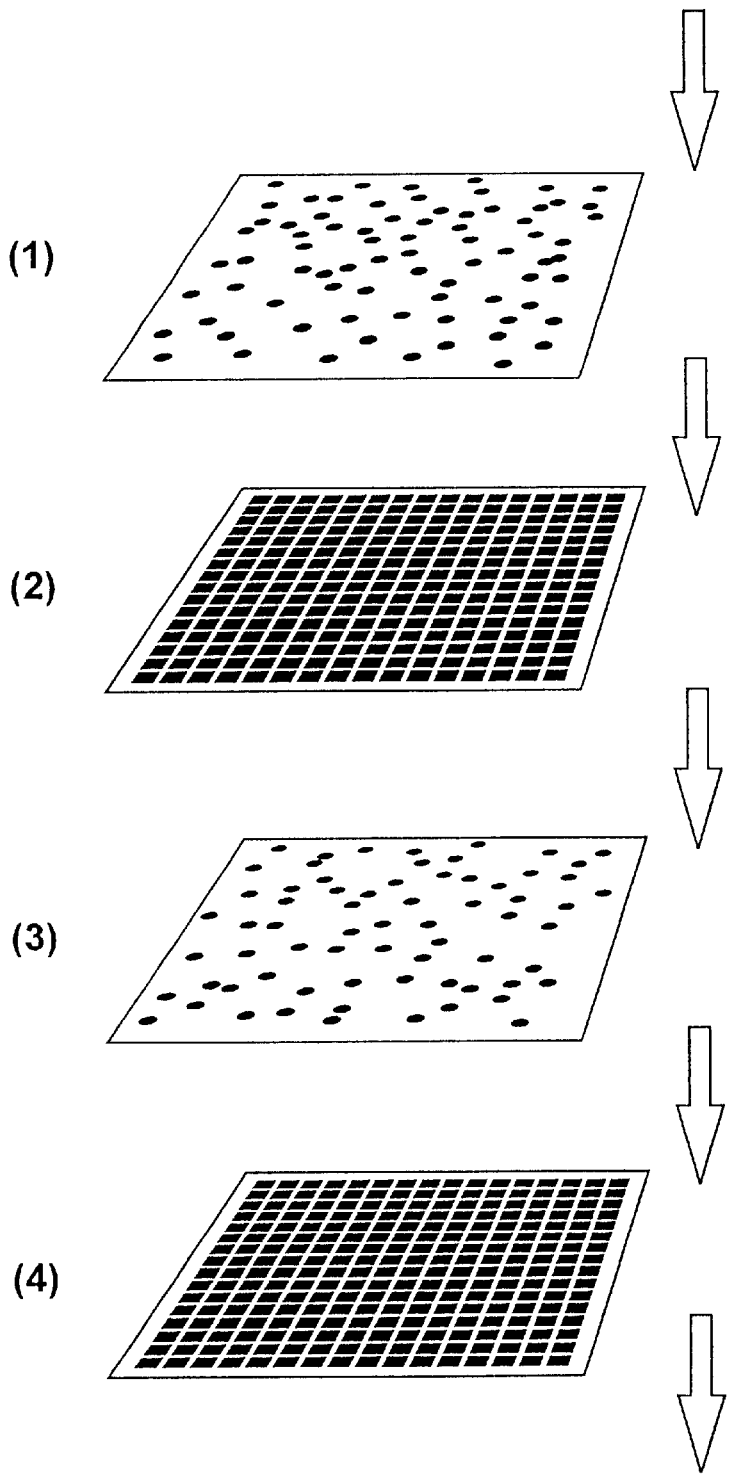
FIG. 9 shows a process for cloning and sequencing genomic fragments.

FIG. 9 shows a process for cloning and sequencing genomic fragments:

(1) following restriction-digesting the DNA fragments are ligated with two different linkers, which specify the sequence of the primers A and B to be used, the genomic fragments are singled out in accordance with the process shown in FIG. 3A; (In the propagation process only those fragments are amplified which carry the various linkers)

(2) the fragments that are singled out and amplified are sorted by means of hybridization ("chromosome walking");

(3) the sorted fragments are propagated individually, split with the use of restriction endonucleases, and subcloned; and (4) the subcloned fragments can again be sorted using hybridization techniques.

Figure 10:
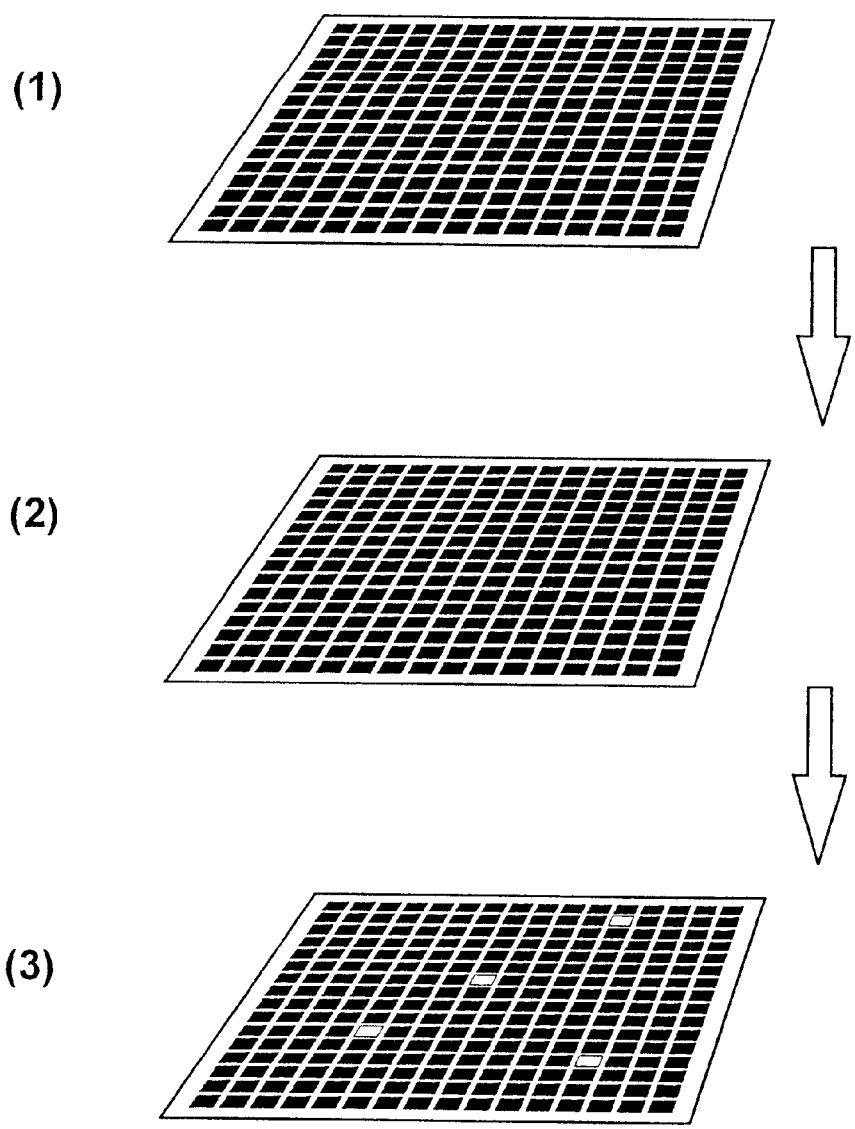
FIG. 10 shows a process for the functional analysis of genomic fragments.

FIG. 10 shows a process for the functional analysis of genomic fragments.

(1) DNA fragments are sorted, as described in FIG. 9;

(2) the single-stranded fragments are augmented by chemical or enzymatic synthesis to produce double strands; and (3) the fragments are brought into contact with factors (e.g. repressor proteins, activator proteins). Proof of specific binding with specific fragments of nucleic acids enables a functional allocation to take place, in a genomic context.

Figure 11:
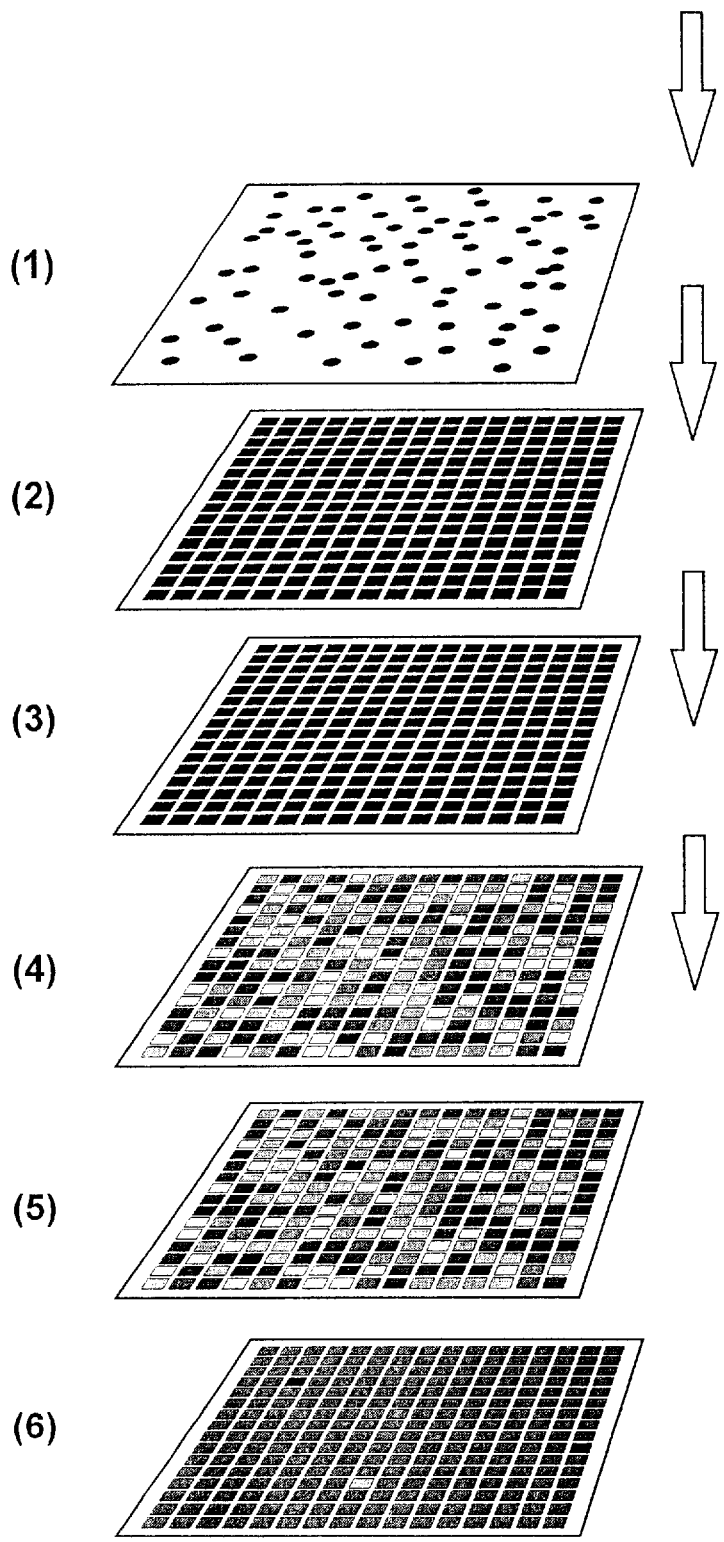
FIG. 11 shows a process for the parallel quantifying of the gene expression.

FIG. 11 shows a process for the parallel quantifying of the gene expression.

(1) following reverse transcription from mRNA, the DNA fragments are provided with linkers and are singled out, as described in FIG. 9;

(2) the cDNA fragments are sorted;

(3) the cDNA fragments are sequenced;

(4) copies of the sorted and sequenced libraries are brought into contact with cellular mRNAs from a healthy cell. The specific hybridization events are confirmed using known, state-of-the-art processes (e.g. fluorescent reporter groups);

(5) in an analog manner the cellular mRNAs from a pathologically altered cell (e.g. a tumorous cell) are brought into contact with another copy of the library; and (6) a comparison of gene expression samples that have been quantified in this way enables identification to be made of the gene associated with the disease.

Figure 12:
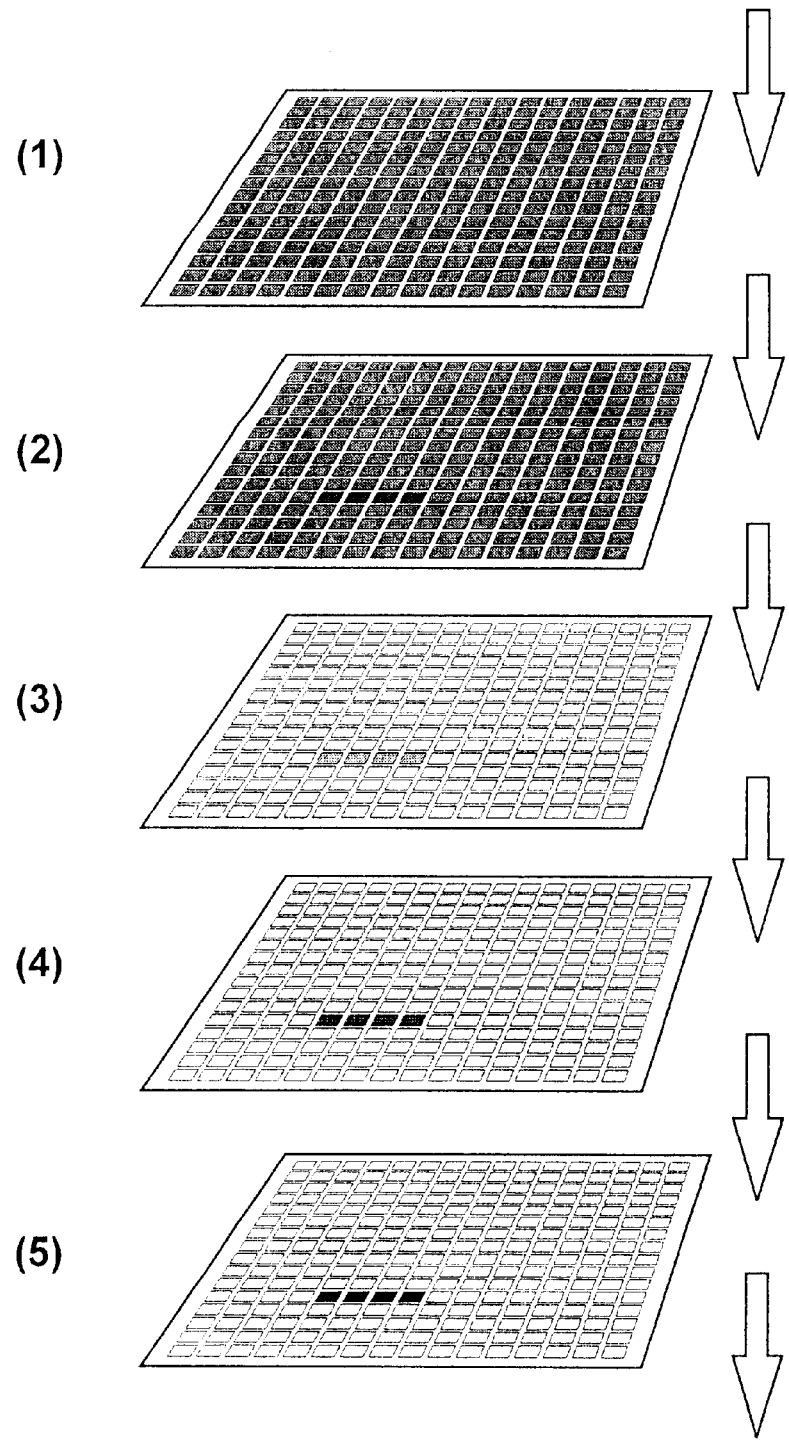
FIG. 12 shows the use of a process as a means of improving the signal-to-noise ratio in the detection process.

FIG. 12 shows the use of the process as a means of improving the signal-to-noise ratio in the detection process:

(1) a library is set up in accordance with the process described in FIG. 9 or 11;

(2) the library is brought into contact with the single-stranded DNA or RNA to be analyzed;

(3) the hybridizing DNAs or RNAs are transferred to the opposite surface, while retaining the site information;

(4) steps 2 and 3 are repeated; and (5) step 4 can be carried out or repeated any number of times. Signal measurement can be conducted using sensitive scanning techniques such as scanning electrochemical microscopy (SECM) or atomic force microscopy (AFM).

Figure 13:
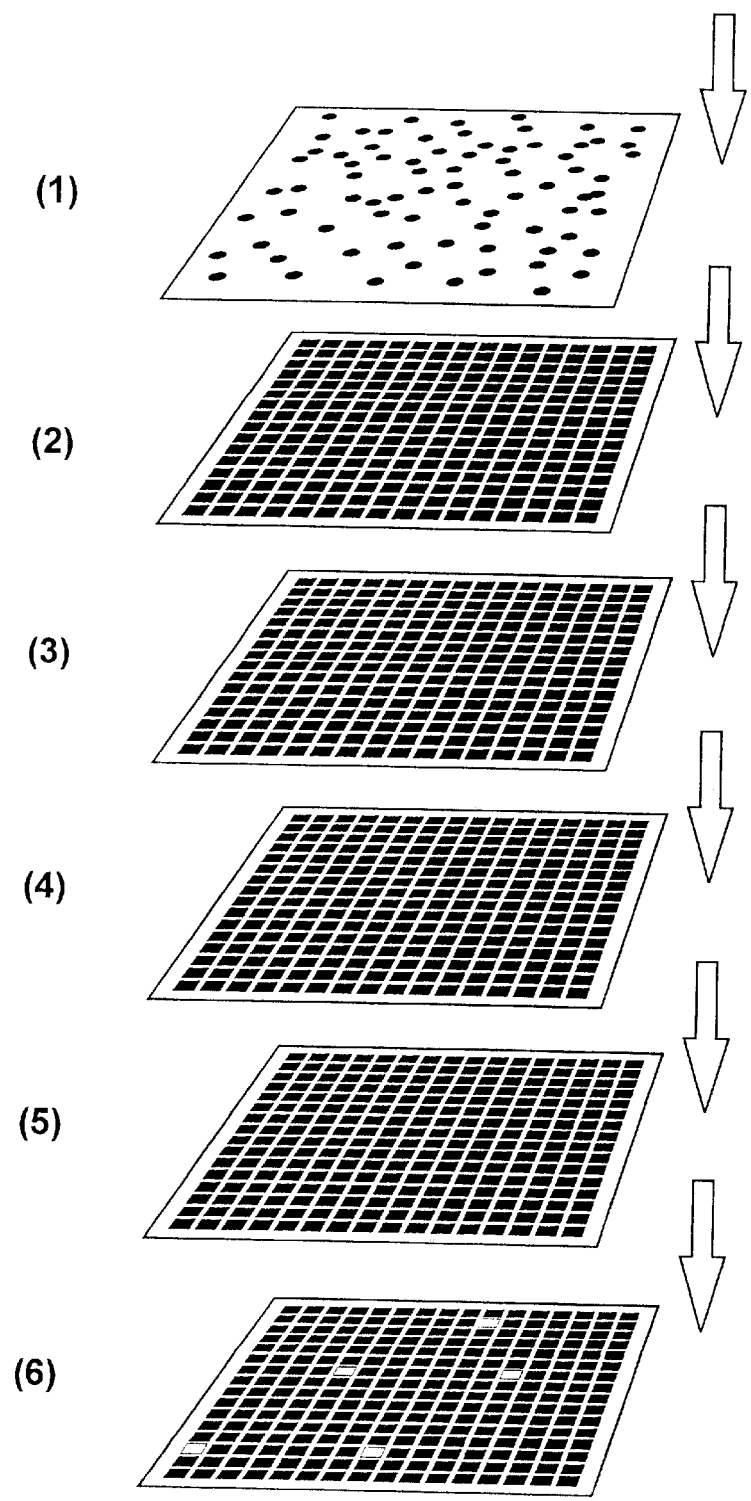
FIG. 13 shows a process used for the functional location of proteins.

FIG. 13 shows the process when used for the functional allocation of proteins:

(1) a library is compiled in accordance with the process described in FIG. 9 or FIG. 11, in which one of the two linkers used contains a starter sequence for an RNA polymerase; (The promoter can also be added afterwards by means of the process described in FIG. 7)

(2) the DNA fragments are sorted;

(3) chemical or enzymatic synthesis is used to make the single-stranded fragments into double-strands;

(4) in-vitro transcription is used to translate the double-stranded DNA fragments into RNA, the RNAs thus created are transferred to a new surface by the application of an electrical field and the provision of site information; and (5) the RNA library is translated into proteins by in-vitro translation, the proteins thus created are transferred to a new surface by the application of an electrical field with the preservation of site information: (Because proteins may possess widely differing net charges, it is preferable to repeat the in-vitro translation stage, carrying out the transfer stage with reversed polarity) The protein library is brought into contact with one or more factors (proteins, RNAs, DNAs, other molecules with a biological or chemical origin). The specific binding events are demonstrated by known, state-of-the-art processes. Proof of the specific binding permits the simultaneous detection of functional interactions.

Figure 14:
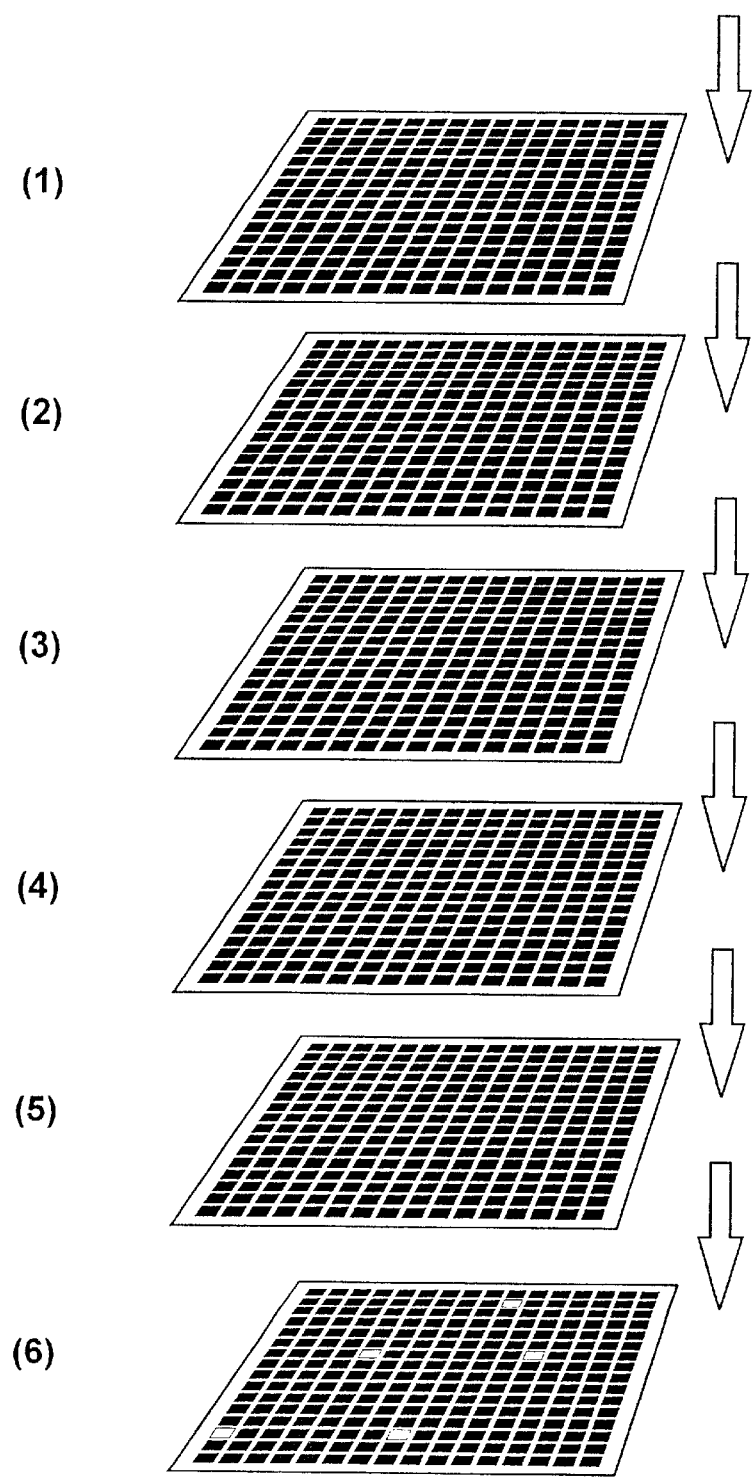
FIG. 14 shows a process used to screen combinatory protein libraries.

FIG. 14 shows how the process is used to screen combinatory protein libraries:

(1) a library of oligonucleotides is produced by chemical synthesis in accordance with known, state-of-the-art processes;

(2) the library of oligonucleotides is extended in the direction of the 3'- and 5'-terminals by means of the process described in FIG. 7; (The extending sequences provide codes, for example for the constant regions of a single chain antibody)

(3) chemical or enzymatic synthesis is used to make the single-stranded fragments into double-strands;

(4) in-vitro transcription is used to translate the double-stranded DNA fragments into RNA, the RNAs thus created are transferred to a new surface by the application of an electrical field and the preservation of site information;

(5) the RNA library is translated into proteins by in-vitro translation, the proteins thus created are transferred to a new surface by the application of an electrical field and the provision of site information; and (6) the protein library is brought into contact with one or more factors (proteins, RNAs, DNAs, other molecules with a biological or chemical origin). The specific binding events are demonstrated by known, state-of-the-art processes. Proof of the specific binding permits the simultaneous detection of functional interactions.

Various features and advantages of the present invention are further illustrated by the following non-limiting example.

EXAMPLE I

The invention is explained using the following working example, i.e. a process for propagating nucleic acids on two surfaces: Synthesis of the primer A led to a biotin label at its 5' end, whereas the primer B received a fluorescein label at its 5' end. The labels were produced in accordance with the usual state-of-the-art methods, for example phosphoamide chemistry. Primer A was coupled with a membrane A. A paper membrane was used as the surface, since this is known to allow the permeation of nucleic acids.

Covalent, coupled streptavidin was applied to this membrane. The coupling took place through the reciprocal action between the biotin and streptavidin. A DNA strand that is complementary to primer A was hybridized on this primer A. The primer A was extended at the 3' end with taq-polymerase or with the Klenow fragment of the polymerase 1. Subsequent denaturing was carried out by heating to 90° C. (alternatively denaturing can also be carried out using a common denaturing reagent). To hybridize the primer B the denaturing solution was replaced by a solution containing TRIS-borate-EDTA-buffers. The primer B was then also extended in the same way as primer A (see also FIGS. 3 and 4).

Using standard electrophoresis apparatus the membrane A was placed on a gel, PAGE gel being preferred. Previously a membrane B was applied to the reverse of the gel, on which fluorescein antibodies had been immobilized. This "sandwich" was held mechanically in a frame, where it was stabilized, and then placed in an electrophoresis chamber designed to ensure separation of both buffers, i.e. the sandwich separates the anode and cathode compartments. A voltage was applied to match the thickness of the gel (in this case 300 v), and subsequently a denaturing agent was flushed into the electrolyte in the (−)-compartment (e.g. a solution of urea). After being heated to 70° C. electrophoresis was carried out. This caused the extended primer B to become detached and travel through the gel layer on the membrane B, where it was subsequently bound and immobilized by binding onto the fluorescein antibodies.

The sandwich was then removed from the electrophoresis chamber, the membranes were removed from the gel, and in accordance with the method described previously, the primer A was again hybridized and extended. Both membranes were then laid on a fresh PAGE gel shaped to enable both membranes to fit accurately in their original orientation, retaining the site information. Then, as described above, electrophoresis was carried out, but in such a way that the membrane B, previously in the (+) compartment (anode compartment), was now allocated to the (−) compartment (cathode compartment).

Alternatively the experiment can be carried out in a microfluid apparatus, in which the membranes and electrodes are firmly positioned, whereas the anode and cathode compartments are flushed out separately and can be flushed using the corresponding reagent. The weakly cross-linked gels that are commonly used in capillary electrophoresis are used in this apparatus. The gels are then replaced for each process.

Alternatively the experiment can also be carried out using activatable reactive primers. In the context of this invention, activatable reactive primers are understood as those possessing a reactive function, and whose reactivity can be influenced by the choice of suitable external conditions. These external conditions may be of a chemical, electrochemical or photochemical nature. An oligonucleotide possessing a cysteine unit via an amino linker whose thiol group is protected in the form of a 2-thiopyrideisulphide group is one example of an activatable reactive primer. In this case the membrane contains carboxy groups in the form of reactive thioesters. Redox-neutral reaction conditions are used in hybridization. After traveling through the field the extended primer reaches a membrane on or in which reductive conditions apply. Reductive conditions are created by the presence, for example, of thiols such as dithioerytrol or dithiothreitol. Disulphide replacement reactions occur in the presence of these reagents, leading to the splitting off of 2-thiopyridons, with the result that the thiol groups released in this way can react on the extended primer with the thioester on the membrane. This reaction initially leads to the formation of a thioester which, due to the presence of the adjacent intramolecular amino group of the cysteine, reacts to form an amide.

One feature of the invention resides broadly in a method for propagating ligands and receptors on at least two surfaces, encompassing one or more of the following cycles: a) Immobilization of a ligand on a first surface of a solid phase; b) Adding a solution of receptors and binding complementary receptors to the ligands; c) Transferring the receptor to an additional surface and immobilizing the receptor at that location; d) Attaching an additional ligand to the immobilized receptor; e) Transferring the ligand to a surface and immobilizing it at that location.

Another feature of the invention resides broadly in a method according to Claim 1, in which the surface in stage (c) and (e) is a second surface which is spatially separated from the first.

Yet another feature of the invention resides broadly in a method in which the transfer in stage (c) and (e) is achieved by the application of an electrical field.

Still another feature of the invention resides broadly in a method in which the electrical field is applied between the first and second surface.

A further feature of the invention resides broadly in a method for the enzymatic propagation of nucleic acids on at least two surfaces, encompassing one or more of the following amplification cycles: a) Immobilization of a first primer on one of the first surfaces of a solid phase; b) Administration of a solution of nucleic acids and binding of complementary fragments to the first primer; c) Extension of the first primer at its 3' end, corresponding to the complementary fragment, by means of a polymerase; d) Release of the complementary fragments; e) Attaching a second primer to the 3' end of the extended nucleic acid; f) Extension of the second primer at its 3' end by means of a polymerase; g) Transfer of the second primer to another surface and immobilization of the extended primer; h) Attaching another first primer to the 3' end of the second, extended primer; Another feature of the invention resides broadly in a method in which the surface in stage (g) is a second surface which is spatially separated from the first.

Yet another feature of the invention resides broadly in a method in which the transfer in stage (g) is achieved by the application of an electrical field.

Still another feature of the invention resides broadly in a method in which the electrical field is applied between the first and second surface.

A further feature of the invention resides broadly in a method in which the following amplification stages occur following the transfer to the second surface: a) Extension of this first primer to its 3' end, corresponding to the complementary fragment, by means of a polymerase; b) Transfer of the extended primer to the first or another surface and immobilization of the primer; c) Attachment of another second primer to the 3' end of the extended first primer.

Another feature of the invention resides broadly in a method for copying nucleic acids from a first to a second surface, encompassing the following stages of the method: a) Immobilization of nucleic acids through a reaction with the surface of a solid carrier; b) Production of double-stranded molecules by hybridization of complementary single strands; or c) chemical or enzymatic ligation of complementary fragments; d) chemical or enzymatic extension of complementary primers; e) Transfer of complementary strands to a second surface, and their immobilization.

Yet another feature of the invention resides broadly in a method in which the transfer in stage (c) occurs by the application of an electrical field, in which the electrical field is applied between the first and second surface.

Still another feature of the invention resides broadly in a method in which the nucleic acids on the solid carrier are arranged two-dimensionally and are transferred in this order, while retaining site information.

A further feature of the invention resides broadly in a method in which the solid phase material is selected from organic or anorganic material or from a hybrid of these materials, and represents a two- or three-dimensional matrix.

Another feature of the invention resides broadly in a method in which the immobilization takes place through covalent or non-covalent binding.

Yet another feature of the invention resides broadly in a method in which the nucleic acids, ligands, receptors or their derivatives are provided with a detectable label.

Still another feature of the invention resides broadly in a method in which the label is selected from the group of radioisotopes, stable isotopes, enzymes, immunoreactive compounds, fluorescence or luminescence chemicals, chromophores, metals or charged particles.

A further feature of the invention resides broadly in a method according to at least one of the previous claims, in which the solution of nucleic acids includes D- and/or L-nucleic acids.

Yet another feature of the invention resides broadly in a method according to at least one of the previous claims, in which an intermediate layer that can be permeated by nucleic acids and/or ligands/receptors is placed between the surfaces.

Still another feature of the invention resides broadly in a method in which the intermediate layer is selected from the group comprising a gel, a membrane, a polymer, a ceramic and/or a co-called capillary tube array.

A further feature of the invention resides broadly in a method in which the nucleic acids are provided with a positively charged group of headings.

Another feature of the invention resides broadly in a method in which, during the respective transfer stage within the respective method sequence, the scale can be reduced and/or increased, while retaining the site information.

Yet another feature of the invention resides broadly in the use of the method according to Claims 5 to 9 for cloning genomic fragments of DNA, cDNA und RNA.

Still another feature of the invention resides broadly in the use for subcloning following restriction-digesting.

A further feature of the invention resides broadly in the use of the method for strengthening an immunological ligand/receptor pair.

Another feature of the invention resides broadly in the use of the method for strengthening the ligand signal.

Yet another feature of the invention resides broadly in the use of the method for sorting adjacent fragments by using hybridization techniques (chromosome walking).

Still another feature of the invention resides broadly in the use of the method for the copying of gene chips.

The components disclosed in the various publications, disclosed or incorporated by reference herein, may be used in the embodiments of the present invention, as well as equivalents thereof.

The appended drawings in their entirety, including all dimensions, proportions and/or shapes in at least one embodiment of the invention, are accurate and are hereby included by reference into this specification.

All, or substantially all, of the components and methods of the various embodiments may be used with at least one embodiment or all of the embodiments, if more than one embodiment is described herein.

All of the patents, patent applications and publications recited herein, and in the Declaration attached hereto, are hereby incorporated by reference as if set forth in their entirety herein.

The corresponding foreign and international patent publication applications, namely, Federal Republic of Germany Patent Application No. 198 54 946.6, filed on Nov. 27, 1998, entitled KOPIEREN UND KLONIEREN AN OBERFLÄCHEN, having inventors Jens Peter FÜRSTE, Sven KLUSSMANN, and Thomas KLEIN, and DE-OS 198 54 946.6, having inventors Jens Peter FÜRSTE, Sven KLUSSMANN, and Thomas KLEIN, and DE-PS 198 54 946.6, having inventors Jens Peter FÜRSTE, Sven KLUSSMANN, and Thomas KLEIN, and International Application No. PCT/DE99/03856, entitled KOPIEREN UND KLONIEREN AN OBERFLÄCHEN, filed on Nov. 26, 1999, having inventors Jens Peter FÜRSTE, Sven KLUSSMANN, and Thomas KLEIN, as well as their published equivalents, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein. All the patents, patent applications and publications anywhere in the present application, such as the references and documents cited in any of the documents cited herein, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

What is claimed is:

1. A method for propagating ligands and receptors on at least two surfaces, comprising one or more of the following cycles:
   (a) immobilizing a first ligand on a first surface of a solid phase;
   (b) adding a solution of receptors and binding complementary receptors to the first ligand;
   (c) transferring the receptor to a location on a second surface and immobilizing the receptor at that location;
   (d) attaching an additional ligand to the immobilized receptor; and
   (e) transferring the additional ligand to the first surface and immobilizing it at that location, wherein the steps set forth above may be repeated multiple times.

2. The method according to claim 1, wherein the transfer in stage (c) and (e) is achieved by the application of an electrical field.

3. The method according to claim 2, wherein the electrical field is applied between the first and second surface.

4. The method according to claim 1, wherein the solid phase is selected from a member of the group consisting of organic or inorganic material or from a hybrid of these materials, and represents a two- or three-dimensional matrix.

5. A method for strengthening an immunological ligand/receptor pair, comprising one or more of the following cycles:
   (a) immobilizing a first ligand on a first surface of a solid phase;
   (b) adding a solution of receptors and binding complementary receptors to the first ligand;
   (c) transferring the receptor to a location on a second surface and immobilizing the receptor at that location;
   (d) attaching an additional ligand to the immobilized receptor; and
   (e) transferring the additional ligand to the first surface and immobilizing it at that location, thus strengthening an immunological ligand/receptor pair, wherein the steps set forth above may be repeated multiple times.

6. A method for strengthening a ligand signal, comprising one or more of the following cycles:
   (a) immobilizing a first ligand on a first surface of a solid phase;
   (b) adding a solution of receptors and binding complementary receptors to the first ligand;
   (c) transferring the receptor to a location on a second surface and immobilizing the receptor at that location;
   (d) attaching an additional ligand to the immobilized receptor; and
   (e) transferring the additional ligand to the first surface and immobilizing it at that location, thus strengthening an ligand/signal, wherein the steps set forth above may be repeated multiple times.

7. A method for the enzymatic propagation of a nucleic acid sequence on at least two surfaces, comprising:
   (a) immobilizing a first primer on at least one first surface of a solid phase;
   (b) administering a solution of nucleic acids comprising complementary fragments to the first primer;
   (c) binding of complementary fragments to the first primer;
   (d) extending the first primer at its 3' end, corresponding to the complementary fragment by means of a polymerase;
   (e) releasing the complementary fragments;
   (f) attaching a second primer to the 3' end of the extended nucleic acid;
   (g) extending the second primer at its 3' end by means of a polymerase;
   (h) transferring the second primer to another surface and immobilization of the extended primer; and
   (i) attaching another first primer to the 3' end of the second extended primer for further extending of the first primer.

8. The method according to claim 7, wherein the surface in step (h) is a second surface which is spatially separated from the first.

9. The method according to claim 7, wherein the transfer in step (h) is achieved by the application of an electrical field.

10. The method according to claim 9, wherein the electrical field is applied between the first and second surface.

11. The method according to claims 7, further comprising the following amplification steps
   (j) extending this first primer to its 3' end, corresponding to the complementary fragment, by means of a polymerase;
   (k) transferring of the extended primer to the first or another surface and immobilization of the extended primer thereon; and
   (l) attaching of another second primer to the 3' end of the extended first primer.

12. A method for cloning genomic fragments of DNA, cDNA and RNA, comprising:
   (a) immobilizing a first primer on at least one first surface of a solid phase;
   (b) administering a solution of nucleic acids comprising complementary fragments to the first primer;
   (c) binding of complementary fragments to the first primer;
   (d) extending the first primer at its 3' end, corresponding to the complementary fragment by means of a polymerase;
   (e) releasing the complementary fragments;
   (f) attaching a second primer to the 3' end of the extended nucleic acid;
   (g) extending the second primer at its 3' end by means of a polymerase;
   (h) transferring the second primer to another surface and immobilization of the extended primer;
   (i) attaching another first primer to the 3' end of the second extended primer for further extending of the first primer;
   (j) extending this first primer to its 3' end, corresponding to the complementary fragment, by means of a polymerase;
   (k) transferring of the extended primer to the first or another surface and immobilization of the extended primer and (m) cloning fragments produced by the above steps thereon;
   (l) attaching of another second primer to the 3' end of the extended first primer.

13. The method according to claim 11, wherein the nucleic acids on the solid phase surface are arranged two-dimensionally and are transferred in this order, while retaining site information.

14. The method according to claim 11, wherein the solid phase surface is selected from a member of the group consisting of organic or inorganic material or from a hybrid of these materials, and represents a two- or three-dimensional matrix.

15. The method according to claims 11, wherein immobilization on the solid phase takes place through covalent or non-covalent binding.

16. The method according to claim 7, where the nucleic acids are provided with a detectable label.

17. The method according to claim 16, wherein the label is selected from a member of the group consisting of radioisotopes, stable isotopes, enzymes, immunoreactive compounds, fluorescence or luminescence chemicals, chromophores, metals or charged particles.

18. The method according to claim 7, wherein the nucleic acids include D- and/or L-nucleic acids.

19. The method according to claim 7 wherein an intermediate layer is placed between the surfaces.

20. The method according to claim 19, wherein the intermediate layer is selected from the group consisting of gel, a membrane, a polymer, a ceramic and capillary tube array.

21. The method according to claim 7, wherein the nucleic acids are each provided with a positive charge.

22. A method for sorting adjacent fragments by using hybridization techniques, comprising:

(a) immobilizing a first primer on at least one first surface of a solid phase;

(b) administering a solution of nucleic acids comprising complementary fragments to the first primer;

(c) binding of complementary fragments to the first primer;

(d) extending the first primer at its 3' end, corresponding to the complementary fragment by means of a polymerase;

(e) releasing the complementary fragments;

(f) attaching a second primer to the 3' end of the extended nucleic acid;

(g) extending the second primer at its 3' end by means of a polymerase;

(h) transferring the second primer to another surface and immobilization of the extended primer;

(i) attaching another first primer to the 3' end of the second extended primer for further extending of the first primer;

(j) extending this first primer to its 3' end, corresponding to the complementary fragment, by means of a polymerase;

(k) transferring of the extended primer to the first or another surface and immobilization of the extended primer thereon;

(l) attaching of another second primer and (m) sorting adjacent fragments produced by the above steps to the 3' end of the extended first primer.

* * * * *

UNITED STATES PATENT AND TRADEMARK OFFICE
CERTIFICATE OF CORRECTION

PATENT NO.    : 6,534,271 B2
DATED         : March 18, 2003
INVENTOR(S)   : Jens Peter Fürste et al.

It is certified that error appears in the above-identified patent and that said Letters Patent is hereby corrected as shown below:

Column 25,
Line 38, before "ligand", delete "an" and insert -- a --.

Column 26,
Lines 41 and 42, after "primer", delete "and (m) cloning fragments produced by the above steps thereon;" and insert -- thereon; --.
Line 44, after "primer", delete "." and insert -- ; and (m) cloning fragments produce by the above steps. --.

Column 28,
Lines 16 and 17, after "primer", delete "and (m) sorting adjacent fragments produced by the above steps".
Line 18, after "primer", delete "." and insert -- ; and (m) sorting adjacent fragments produce by the above steps. --.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,534,271 B2
DATED         : March 18, 2003
INVENTOR(S)   : Jens Peter Fürste et al.

It is certified that error appears in the above-identified patent and that said Letters Patent is hereby corrected as shown below:

Column 26,
Line 44, after "fragments", delete "produce" and insert -- produced --.

Column 28,
Line 18, after "fragments", delete "produce" and insert -- produced --.

Signed and Sealed this

Sixteenth Day of December, 2003

JAMES E. ROGAN
*Director of the United States Patent and Trademark Office*